United States Patent
Freudiger et al.

(10) Patent No.: US 12,161,486 B2
(45) Date of Patent: Dec. 10, 2024

(54) IMAGING SYSTEM FOR DETECTION OF INTRAOPERATIVE CONTRAST AGENTS IN TISSUE

(71) Applicant: INVENIO IMAGING, INC., Santa Clara, CA (US)

(72) Inventors: Christian Wilhelm Freudiger, Santa Clara, CA (US); Balaji Pandian, Santa Clara, CA (US); Jay Trautman, Santa Clara, CA (US)

(73) Assignee: INVENIO IMAGING, INC., Santa Clara, CA (US)

( * ) Notice: Subject to any disclaimer, the term of this patent is extended or adjusted under 35 U.S.C. 154(b) by 399 days.

(21) Appl. No.: 17/491,844

(22) Filed: Oct. 1, 2021

(65) Prior Publication Data

US 2022/0087532 A1 Mar. 24, 2022

Related U.S. Application Data

(63) Continuation of application No. PCT/US2020/027830, filed on Apr. 10, 2020.

(Continued)

(51) Int. Cl.
*A61B 5/00* (2006.01)
*A61K 49/00* (2006.01)
(Continued)

(52) U.S. Cl.
CPC .......... *A61B 5/7267* (2013.01); *A61B 5/0068* (2013.01); *A61B 5/0071* (2013.01);
(Continued)

(58) Field of Classification Search
CPC . A61B 2576/00; A61B 5/0033; A61B 5/0035; A61B 5/0068; A61B 5/0071;
(Continued)

(56) References Cited

U.S. PATENT DOCUMENTS 6,555,811 B1 4/2003 Amos
8,792,156 B1 7/2014 Kieu et al.
(Continued)

FOREIGN PATENT DOCUMENTS

JP 2018185265 A 11/2018
WO WO-2017053825 A1 3/2017
(Continued)

OTHER PUBLICATIONS

Bueno, et al. Second harmonic generation microscopy: a tool for quantitative analysis of tissues. Microscopy and Analysis (2016): 99-119.
(Continued)

*Primary Examiner* — Amelie R Davis
(74) *Attorney, Agent, or Firm* — WILSON SONSINI GOODRICH & ROSATI

(57) ABSTRACT

Systems and methods are described for using a combination of high-resolution, optical-sectioning imaging modalities to provide quantitative measures of the distribution of a contrast agent in tissue samples by identifying its cellular distribution. In some instances, the systems and methods may be used in an intraoperative setting to guide a biopsy or surgical procedure.

19 Claims, 10 Drawing Sheets

Laser scanning microscope

Related U.S. Application Data

(60) Provisional application No. 62/833,553, filed on Apr. 12, 2019.

(51) Int. Cl.
*G02B 21/00* (2006.01)
*G06T 7/00* (2017.01)
*G06T 7/70* (2017.01)
*G06V 10/42* (2022.01)
*G06V 10/44* (2022.01)
*G06V 10/48* (2022.01)
*G06V 10/762* (2022.01)
*G06V 10/764* (2022.01)
*G06V 10/774* (2022.01)
*G06V 10/82* (2022.01)
*G06V 20/69* (2022.01)

(52) U.S. Cl.
CPC ...... *A61K 49/0021* (2013.01); *G02B 21/0076* (2013.01); *G02B 21/008* (2013.01); *G06T 7/0012* (2013.01); *G06T 7/70* (2017.01); *G06V 10/431* (2022.01); *G06V 10/454* (2022.01); *G06V 10/48* (2022.01); *G06V 10/762* (2022.01); *G06V 10/764* (2022.01); *G06V 10/774* (2022.01); *G06V 10/82* (2022.01); *G06V 20/69* (2022.01); *G06V 20/693* (2022.01); *A61B 2576/00* (2013.01); *G06T 2207/10056* (2013.01); *G06T 2207/10064* (2013.01); *G06T 2207/20081* (2013.01); *G06T 2207/30242* (2013.01)

(58) Field of Classification Search
CPC .............. A61B 5/0075; A61B 5/7267; G02B 21/0012; G02B 21/0064; G02B 21/0076; G02B 21/008; G02B 21/367; G06T 2207/10056; G06T 2207/10064; G06T 2207/20081; G06T 2207/20084; G06T 2207/30016; G06T 2207/30242; G06T 7/0012; G06V 10/764; G06V 10/762; G06V 20/69

See application file for complete search history.

(56) References Cited

U.S. PATENT DOCUMENTS

| | | | |
|---|---|---|---|
| 9,104,030 B2 | 8/2015 | Kieu et al. | |
| 9,634,454 B1 | 4/2017 | Kieu et al. | |
| 10,416,434 B2 | 9/2019 | Fujimoto et al. | |
| 2004/0010192 A1* | 1/2004 | Benaron | A61B 5/0075 600/431 |
| 2006/0013454 A1* | 1/2006 | Flewelling | G06T 11/00 382/128 |
| 2008/0262384 A1 | 10/2008 | Wiederkehr et al. | |
| 2011/0317258 A1 | 12/2011 | Wolleschensky | |
| 2014/0193833 A1 | 7/2014 | Srivastava et al. | |
| 2014/0285873 A1* | 9/2014 | Kieu | G02F 1/353 359/328 |
| 2015/0119722 A1* | 4/2015 | Kaneko | A61B 1/043 600/476 |
| 2017/0350805 A1* | 12/2017 | Murata | G01N 21/27 |
| 2018/0074306 A1* | 3/2018 | Visscher | G06T 3/153 |
| 2018/0259762 A1 | 9/2018 | Fujimoto et al. | |
| 2018/0286040 A1* | 10/2018 | Sashida | G06F 18/2414 |
| 2018/0348496 A1 | 12/2018 | Brown | |
| 2019/0223728 A1* | 7/2019 | Heidari | G06V 10/82 |
| 2021/0210169 A1* | 7/2021 | Meyer | G06V 10/40 |

FOREIGN PATENT DOCUMENTS

| | | |
|---|---|---|
| WO | WO-2018125925 A1 | 7/2018 |
| WO | WO-2018218150 A1 | 11/2018 |
| WO | WO-2019032723 A1 | 2/2019 |
| WO | WO-2020091965 A2 | 5/2020 |
| WO | WO-2020091965 A3 | 6/2020 |
| WO | WO-2020210746 A1 | 10/2020 |
| WO | WO-2023278779 A1 | 1/2023 |

OTHER PUBLICATIONS

Butte, et al. Near-infrared imaging of brain tumors using the Tumor Paint BLZ-100 to achieve near-complete resection of brain tumors. Neurosurg Focus. Feb. 2014;36(2):E1.

Crisafi et al. Multimodal Nonlinear Microscope based on a Compact Fiber-format Laser Source, arXiv:1707.04545 submitted Jul. 14, 2017.

Dietzel, Steffen. Third Harmonic Generation Microscopy. Imaging & Microscopy. Nov. 11, 2014.

Fidel, et al. Preclinical Validation of the Utility of BLZ-100 in Providing Fluorescence Contrast for Imaging Spontaneous Solid Tumors. Cancer Res. 75, 4283-4291 (2015).

Gonzalez, et al. Real-time, in vivo confocal reflectance microscopy of basal cell carcinoma. Journal of the American Academy of Dermatology 47.6 (2002): 869-874.

Isobe, et al. Simultaneous imaging of two-photon absorption and stimulated Raman scattering by spatial overlap modulation nonlinear optical microscopy. Biomedical optics express 4.9 (2013): 1548-1558.

Kaneko, et al. Fluorescence-guided resection of malignant glioma with 5-ALA. International journal of biomedical imaging 2016 (2016).

Lee, et al. In vivo imaging of the tumor and its associated microenvironment using combined CARS/2- photon microscopy. IntraVital 4.1 (2015).

Li, et al. Integrated femtosecond stimulated Raman scattering and two-photon fluorescence imaging of subcellular lipid and vesicular structures. Journal of biomedical optics 20.11 (2015): 110501.

Liu, et al. Trends in fluorescence image-guided surgery for gliomas. Neurosurgery 75.1 (2014): 61-71.

Meyer, et al. Nonlinear microscopy, infrared, and Raman microspectroscopy for brain tumor analysis. Journal of biomedical optics 16.2 (2011): 021113.

PCT/US2020/027830 International Search Report dated Jul. 9, 2020.

Smith, et al. Real-time, intraoperative detection of residual breast cancer in lumpectomy cavity walls using a novel cathepsin-activated fluorescent imaging system. Breast cancer research and treatment 171.2 (2018): 413-420.

Szarowski, et al. Optimized reflection imaging in laser confocal microscopy and its application to neurobiology: Modificationsa to the biorad MRC-500. Scanning 14.2 (1992): 104-111.

Wang, et al. Enhancement of 5-aminolevulinic acid-based fluorescence detection of side population-defined glioma stem cells by iron chelation. Scientific reports 7.1 (2017): 1-12.

Whitley, et al. A mouse-human phase 1 co-clinical trial of a protease-activated fluorescent probe for imaging cancer. Science translational medicine 8.320 (2016): 320ra4-320ra4.

Bajcsy, Peter, et al. Survey statistics of automated segmentations applied to optical imaging of mammalian cells. BMC bioinformatics vol. 16, 330 (2015): 1-28.

Camp, Charles H Jr. et al. High-Speed Coherent Raman Fingerprint Imaging of Biological Tissues. Nature photonics vol. 8 (2014): 627-634.

Combs, Christian A. Fluorescence microscopy: a concise guide to current imaging methods. Current protocols in neuroscience vol. Chapter 2 (2010): Unit2.1. doi:10.1002/0471142301.ns0201s50.

Denk, W et al. Two-photon laser scanning fluorescence microscopy. Science (New York, N.Y.) vol. 248,4951 (1990): 73-6. doi:10.1126/science.2321027.

EP20788187.1 Extended European Search Report dated Dec. 13, 2022.

Evans, Conor L et al. Chemically-selective imaging of brain structures with CARS microscopy. Optics express vol. 15,19 (2007): 12076-87. doi:10.1364/OE.15.012076.

(56) References Cited

OTHER PUBLICATIONS

Freudiger, Christian W et al. Label-free biomedical imaging with high sensitivity by stimulated Raman scattering microscopy. Science (New York, N.Y.) vol. 322,5909 (2008): 1857-61.

Glaser, Adam K et al. Light-sheet microscopy for slide-free nondestructive pathology of large clinical specimens. Nature biomedical engineering vol. 1,7 (2017): 0084. doi:10.1038/s41551-017-0084.

Harmsen, Stefan et al. Optical Surgical Navigation for Precision in Tumor Resections. Molecular imaging and biology vol. 19,3 (2017): 357-362.

Meza, Daphne et al. Comparing high-resolution microscopy techniques for potential intraoperative use in guiding low-grade glioma resections. Lasers in surgery and medicine vol. 47,4 (2015): 289-95. doi:10.1002/lsm.22347.

Neil, M. A. A. et al. Method of obtaining optical sectioning by using structured light in a conventional microscope. Opt. Lett. 22 (1997): 1905-1907.

Orringer, Daniel A et al. Rapid intraoperative histology of unprocessed surgical specimens via fibre-laser-based stimulated Raman scattering microscopy. Nature biomedical engineering vol. 1 (2017): 0027. doi:10.1038/s41551-016-0027.

PCT/US2022/035835 International Search Report and Written Opinion dated Oct. 4, 2022.

Sanai, Nader et al. Intraoperative confocal microscopy in the visualization of 5-aminolevulinic acid fluorescence in low-grade gliomas. Journal of neurosurgery vol. 115,4 (2011): 740-8. doi:10.3171/2011.6.JNS11252.

Santi, Peter A. Light sheet fluorescence microscopy: a review. The journal of histochemistry and cytochemistry : official journal of the Histochemistry Society vol. 59,2 (2011): 129-38.

Winfree, Seth, et al. Large-scale 3-dimensional quantitative imaging of tissues: state-of-the-art and translational implications. Translational research: the journal of laboratory and clinical medicine vol. 189 (2017): 1-12.

Yue, Shuhua et al. Multimodal nonlinear optical microscopy. Laser & photonics reviews vol. 5, No. 4 (2011): 496-512.

\* cited by examiner

IMAGING SYSTEM FOR DETECTION OF INTRAOPERATIVE CONTRAST AGENTS IN TISSUE

CROSS-REFERENCE

This application is a Continuation Application of International Patent Application PCT/US2020/027830, filed Apr. 10, 2020, which claims the benefit of U.S. Provisional Application No. 62/833,553, filed Apr. 12, 2019, each of which is incorporated herein by reference in its entirety.

SUMMARY

Disclosed herein are systems for imaging a tissue specimen comprising: a) a first optical sub-system configured to acquire high-resolution images of a distribution of a cell-associated contrast agent within the tissue specimen using a first optical-sectioning imaging modality; b) a second optical sub-system configured to acquire high-resolution images of tissue specimen morphology using a second optical-sectioning imaging modality, wherein the first and second optical sub-systems are configured to image the same optical plane within the tissue specimen; and c) a processor configured to run an image interpretation algorithm that processes the images acquired using either or both of the first and second optical-sectioning imaging modalities to identify individual cells and determine their locations, and outputs a quantitative measure of a signal derived from the cell-associated contrast agent by measuring the signal at the locations corresponding to those of the individual cells in the images acquired using the first imaging modality. In some embodiments, the first optical-sectioning imaging modality comprises two-photon fluorescence microscopy, confocal fluorescence microscopy, light sheet microscopy, or structured illumination microscopy. In some embodiments, the second optical-sectioning imaging modality comprises stimulated Raman scattering microscopy, coherent anti-Stokes Raman scattering microscopy, confocal reflection microscopy, second harmonic generation microscopy, or third harmonic generation microscopy. In some embodiments, the first and second optical sub-systems are configured to have an axial resolution smaller than 10 μm. In some embodiments, the first and second optical sub-systems are configured to have a lateral resolution smaller than 5 μm. In some embodiments, the first optical sub-system is further configured to acquire high resolution images in two or more detection wavelength ranges. In some embodiments, a first detection wavelength range of the two or more detection wavelength ranges includes an emission peak of the cell-associated contrast agent; a second detection wavelength range of the two or more detection wavelength ranges excludes the emission peak of the cell-associated contrast agent; and the image interpretation algorithm further processes images acquired using the first detection wavelength to identify individual cells and determine their locations, and outputs a quantitative measure of the signal derived from the cell-associated contrast agent by measuring the signal at the locations of the individual cells and correcting the signal by a background value measured at locations corresponding to those of the individual cells in the images acquired using the second detection wavelength range. In some embodiments, the second optical-sectioning imaging modality comprises stimulated Raman scattering microscopy, and the images are acquired at a wavenumber of 2,850 $cm^{-1}$ corresponding to the $CH_2$-vibration of lipid molecules. In some embodiments, images are also acquired at a wavenumber of 2,930 $cm^{-1}$ corresponding to the $CH_3$-vibration of protein and nucleic acid molecules. In some embodiments, the signal derived from the cell-associated contrast agent comprises a fluorescence signal, a phosphorescence signal, or any combination thereof. In some embodiments, the cell-associated contrast agent comprises an antibody conjugated to a fluorophore, a quantum dot, a nanoparticle, or a phosphor. In some embodiments, the cell-associated contrast agent comprises a fluorogenic enzyme substrate. In some embodiments, the cell-associated contrast agent comprises fluorescein, 5-ALA, BLZ-100, or LUM015. In some embodiments, the cell-associated contrast agent comprises 5-aminolevulinic acid (5-ALA), wherein the first emission wavelength range includes 640 nm light and the second emission wavelength includes wavelengths shorter than 600 nm. In some embodiments, the image interpretation algorithm comprises a Canny edge detection algorithm, a Canny-Deriche edge detection algorithm, a first-order gradient edge detection algorithm, a second order differential edge detection algorithm, a phase coherence edge detection algorithm, an image segmentation algorithm, and intensity thresholding algorithm, an intensity clustering algorithm, and intensity histogram-based algorithm, a feature recognition algorithm, a pattern recognition algorithm, a generalized Hough transform algorithm, a circular Hough transform algorithm, a Fourier transform algorithm, a fast Fourier transform algorithm, a wavelet analysis algorithm, an auto-correlation algorithm, or any combination thereof. In some embodiments, the image interpretation algorithm detects individual cells based on image feature size, shape, pattern, intensity, or any combination thereof. In some embodiments, the image interpretation algorithm comprises an artificial intelligence or machine learning algorithm. In some embodiments, the image interpretation algorithm comprises a supervised machine learning algorithm, an unsupervised machine learning algorithm, a semi-supervised machine learning algorithm, or any combination thereof. In some embodiments, the machine learning algorithm comprises an artificial neural network algorithm, a deep convolutional neural network algorithm, a deep recurrent neural network, a generative adversarial network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof. In some embodiments, the machine learning algorithm is trained using a training data set comprising imaging data acquired for archived histopathological tissue samples, imaging date acquired for fresh histopathological tissue samples, or any combination thereof. In some embodiments, the training data set is continuously, periodically, or randomly updated with imaging data acquired by two or more systems that have been deployed for use at the same or different sites. In some embodiments, the two or more systems are deployed at different sites, and the training data set is continuously, periodically, or randomly updated via an internet connection. In some embodiments, the image interpretation algorithm determines a total or an average intensity of the signal derived from the cell-associated contrast agent. In some embodiments, the image interpretation algorithm determines whether the signal derived from the cell-associated contrast agent for individual cells is above a specified threshold level for contrast-positive cells. In some embodiments, the image interpretation algorithm outputs a total number of contrast-positive cells within an image of the tissue specimen, a density of contrast-positive cells within an image of the tissue specimen, a percentage of contrast-positive cells within an image of the tissue specimen, or any combination thereof. In some embodiments, the image interpretation algorithm also outputs a cellularity score based on the images acquired using the second optical-sectioning imaging modality. In some embodiments, the images of the tissue specimen are acquired in vivo. In some embodiments, the images of the tissue specimen are acquired ex vivo. In some embodiments, the system is used during a surgical procedure to identify locations for performing a biopsy or to determine if resection is complete.

Also disclosed herein are methods for cellular resolution imaging of a tissue specimen, the methods comprising; a) acquiring high-resolution, optically-sectioned images of a distribution of a cell-associated contrast agent within the tissue specimen using a first imaging modality; b) acquiring high-resolution, optically-sectioned images of tissue specimen morphology within the same optical focal plane within the tissue specimen as that for (a) using a second imaging modality; and c) processing the images acquired using either or both of the first and second imaging modalities using an image interpretation algorithm that identifies individual cells and determines their locations, and outputs a quantitative measure of a signal derived from the cell-associated contrast agent at cellular resolution by measuring the signal at locations corresponding to those of the individual cells in the images acquired using the first imaging modality. In some embodiments, the first imaging modality comprises two-photon fluorescence microscopy, confocal fluorescence microscopy, light sheet microscopy, or structured illumination microscopy. In some embodiments, the second imaging modality comprises stimulated Raman scattering microscopy, coherent anti-Stokes Raman scattering microscopy, confocal reflection microscopy, second harmonic generation microscopy, or third harmonic generation microscopy. In some embodiments, the images acquired using the first imaging modality and the second imaging modality have an axial resolution smaller than 10 µm. In some embodiments, the images acquired using the first imaging modality and the second imaging modality have a lateral resolution smaller than 5 µm. In some embodiments, the method further comprises acquiring images in two or more detection wavelength ranges using the first imaging modality. In some embodiments, a first detection wavelength range of the two or more detection wavelength ranges includes an emission peak of the cell-associated contrast agent; a second detection wavelength range of the two or more detection wavelength ranges excludes the emission peak of the cell-associated contrast agent; and the image interpretation algorithm further processes images acquired using the first detection wavelength to identify individual cells and determine their locations, and outputs a quantitative measure of the signal derived from the cell-associated contrast agent by measuring the signal at the locations of the individual cells and correcting the signal by a background value measured at locations corresponding to those of the individual cells in the images acquired using the second emission wavelength range. In some embodiments, the second imaging modality comprises stimulated Raman scattering microscopy, and the images are acquired at a wavenumber of 2,850 $cm^{-1}$ corresponding to the $CH_2$-vibration of lipid molecules. In some embodiments, images are also acquired at a wavenumber of 2,930 $cm^{-1}$ corresponding to the $CH_3$-vibration of protein and nucleic acid molecules. In some embodiments, the signal derived from the cell-associated contrast agent comprises a fluorescence signal, a phosphorescence signal, or any combination thereof. In some embodiments, the cell-associated contrast agent comprises an antibody conjugated to a fluorophore, a quantum dot, a nanoparticle, or a phosphor. In some embodiments, the cell-associated contrast agent comprises a fluorogenic enzyme substrate. In some embodiments, the cell-associated contrast agent comprises fluorescein, 5-ALA, BLZ-100, or LUM015. In some embodiments, the cell-associated contrast agent comprises 5-aminolevulinic acid (5-ALA), wherein the first emission wavelength range includes 640 nm light and the second emission wavelength includes wavelengths shorter than 600 nm. In some embodiments, the image interpretation algorithm comprises a Canny edge detection algorithm, a Canny-Deriche edge detection algorithm, a first-order gradient edge detection algorithm, a second order differential edge detection algorithm, a phase coherence edge detection algorithm, an image segmentation algorithm, and intensity thresholding algorithm, an intensity clustering algorithm, and intensity histogram-based algorithm, a feature recognition algorithm, a pattern recognition algorithm, a generalized Hough transform algorithm, a circular Hough transform algorithm, a Fourier transform algorithm, a fast Fourier transform algorithm, a wavelet analysis algorithm, an auto-correlation algorithm, or any combination thereof. In some embodiments, the image interpretation algorithm detects individual cells based on image feature size, shape, pattern, intensity, or any combination thereof. In some embodiments, the image interpretation algorithm comprises an artificial intelligence or machine learning algorithm. In some embodiments, the image interpretation algorithm comprises a supervised machine learning algorithm, an unsupervised machine learning algorithm, a semi-supervised machine learning algorithm, or any combination thereof. In some embodiments, the machine learning algorithm comprises an artificial neural network algorithm, a deep convolutional neural network algorithm, a deep recurrent neural network, a generative adversarial network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof. In some embodiments, the machine learning algorithm is trained using a training data set comprising imaging data acquired for archived histopathological tissue samples, imaging date acquired for fresh histopathological tissue samples, or any combination thereof. In some embodiments, the training data set is continuously, periodically, or randomly updated with imaging data acquired by two or more systems that have been deployed for use at the same or different sites. In some embodiments, the two or more systems are deployed at different sites, and the training data set is continuously, periodically, or randomly updated via an internet connection. In some embodiments, the image interpretation algorithm determines a total or an average intensity of the signal derived from the cell-associated contrast agent. In some embodiments, the image interpretation algorithm determines whether the signal derived from the cell-associated contrast agent for individual cells is above a specified threshold level for contrast-positive cells. In some embodiments, the image interpretation algorithm outputs a total number of contrast-positive cells within an image of the tissue specimen, a density of contrast-positive cells within an image of the tissue specimen, a percentage of contrast-positive cells within an image of the tissue specimen, or any combination thereof. In some embodiments, the image interpretation algorithm also outputs a cellularity score based on the images acquired using the second optical-sectioning imaging modality. In some embodiments, the images of the tissue specimen are acquired in vivo. In some embodiments, the images of the tissue specimen are acquired ex vivo. In some embodiments, the method is used during a surgical procedure to identify locations for performing a biopsy or to determine if resection is complete.

Disclosed herein are systems for imaging a tissue specimen comprising: a) a high-resolution optical-sectioning microscope configured to acquire images of the tissue specimen; and b) a processor configured to run an image interpretation algorithm that detects individual cells in the images acquired by the high-resolution optical-sectioning microscope and outputs a quantitative measure of a signal derived from a cell-associated contrast agent. In some embodiments, the high-resolution optical sectioning microscope comprises a two-photon fluorescence microscope, a confocal fluorescence microscope, a light sheet microscope, or a structured illumination microscope. In some embodiments, the high-resolution optical-sectioning microscope has an axial resolution smaller than 10 µm. In some embodiments, the high-resolution optical-sectioning microscope has a lateral resolution smaller than 5 µm. In some embodiments, the high-resolution optical sectioning microscope is configured to acquire images in two or more emission wavelength ranges. In some embodiments, a first emission wavelength range of the two or more detection wavelength ranges includes an emission peak of the cell-associated contrast agent; a second detection wavelength range of the two or more emission wavelength ranges excludes the emission peak of the cell-associated contrast agent; and the image interpretation algorithm processes images acquired using the first detection wavelength range to identify individual cells and determine their locations, and outputs a quantitative measure of the signal derived from the cell-associated contrast agent by measuring the signal at the locations of the individual cells and correcting the signal using a background value measured at corresponding locations in images acquired using the second detection wavelength range. In some embodiments, the signal derived from the cell-associated contrast agent comprises a fluorescence signal, a phosphorescence signal, or any combination thereof. In some embodiments, the cell-associated contrast agent comprises an antibody conjugated to a fluorophore, a quantum dot, a nanoparticle, or a phosphor. In some embodiments, the cell-associated contrast agent comprises a fluorogenic enzyme substrate. In some embodiments, the cell-associated contrast agent comprises fluorescein, 5-ALA, BLZ-100, or LUM015. In some embodiments, the cell-associated contrast agent comprises 5-aminolevulinic acid (5-ALA), wherein the first emission wavelength range includes 640 nm light and the second emission wavelength includes wavelengths shorter than 600 nm. In some embodiments, the image interpretation algorithm comprises a Canny edge detection algorithm, a Canny-Deriche edge detection algorithm, a first-order gradient edge detection algorithm, a second order differential edge detection algorithm, a phase coherence edge detection algorithm, an image segmentation algorithm, and intensity thresholding algorithm, an intensity clustering algorithm, and intensity histogram-based algorithm, a feature recognition algorithm, a pattern recognition algorithm, a generalized Hough transform algorithm, a circular Hough transform algorithm, a Fourier transform algorithm, a fast Fourier transform algorithm, a wavelet analysis algorithm, an auto-correlation algorithm, or any combination thereof. In some embodiments, the image interpretation algorithm detects individual cells based on image feature size, shape, pattern, intensity, or any combination thereof. In some embodiments, the image interpretation algorithm comprises an artificial intelligence or machine learning algorithm. In some embodiments, the image interpretation algorithm comprises a supervised machine learning algorithm, an unsupervised machine learning algorithm, a semi-supervised machine learning algorithm, or any combination thereof. In some embodiments, the machine learning algorithm comprises an artificial neural network algorithm, a network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof. In some embodiments, the machine learning algorithm is trained using a training data set comprising imaging data acquired for archived histopathological tissue samples, imaging date acquired for fresh histopathological tissue samples, or any combination thereof. In some embodiments, the training data set is continuously, periodically, or randomly updated with imaging data acquired by two or more systems that have been deployed for use at the same or different sites. In some embodiments, the two or more systems are deployed at different sites, and the training data set is continuously, periodically, or randomly updated via an internet connection. In some embodiments, the quantitative measure of the signal derived from the cell-associated contrast agent comprises a measure of an amount of contrast agent associated with one or more individual cells in the image. In some embodiments, the quantitative measure of the signal derived from the cell-associated contrast agent comprises a measure of a total number of contrast-positive cells within an image, a density of contrast-positive cells within an image, a percentage of contrast agent positive cells within an image, or any combination thereof. In some embodiments, the images of the tissue specimen are acquired in vivo. In some embodiments, the images of the tissue specimen are acquired ex vivo. In some embodiments, the system is used during a surgical procedure to identify locations for performing a biopsy or to determine if resection is complete.

Disclosed herein are methods for imaging a tissue specimen, the methods comprising: a) acquiring high-resolution, optically sectioned images of the tissue specimen; and b) processing the images using an image interpretation algorithm that detects individual cells in the images and outputs a quantitative measure of a signal derived from a cell-associated contrast agent at a location of one or more individual cells. In some embodiments, the high-resolution, optically-sectioned images are acquired using two-photon fluorescence microscopy, confocal fluorescence microscopy, light sheet microscopy, or structured illumination microscopy. In some embodiments, the first imaging modality comprises two-photon fluorescence microscopy, confocal fluorescence microscopy, light sheet microscopy, or structured illumination microscopy. In some embodiments, the acquired images have an axial resolution smaller than 10 µm. In some embodiments, the acquired images have a lateral resolution smaller than 5 µm. In some embodiments, the signal derived from the cell-associated contrast agent comprises a fluorescence signal, a phosphorescence signal, or any combination thereof. In some embodiments, the cell-associated contrast agent comprises an antibody conjugated to a fluorophore, a quantum dot, a nanoparticle, or a phosphor. In some embodiments, the cell-associated contrast agent comprises a fluorogenic enzyme substrate. In some embodiments, the cell-associated contrast agent comprises fluorescein, 5-ALA, BLZ-100, or LUM015. In some embodiments, the image interpretation algorithm comprises a Canny edge detection algorithm, a Canny-Deriche edge detection algorithm, a first-order gradient edge detection algorithm, a second order differential edge detection algorithm, a phase coherence edge detection algorithm, an image segmentation algorithm, and intensity thresholding algorithm, an intensity clustering algorithm, and intensity histogram-based algorithm, a feature recognition algorithm, a pattern recognition algorithm, a generalized Hough transform algorithm, a circular Hough transform algorithm, a Fourier transform algorithm, a fast Fourier transform algorithm, a wavelet analysis algorithm, an auto-correlation algorithm, or any combination thereof. In some embodiments, the image interpretation algorithm detects individual cells based on image feature size, shape, pattern, intensity, or any combination thereof. In some embodiments, the image interpretation algorithm comprises an artificial intelligence or machine learning algorithm. In some embodiments, the image interpretation algorithm comprises a supervised machine learning algorithm, an unsupervised machine learning algorithm, a semi-supervised machine learning algorithm, or any combination thereof. In some embodiments, the machine learning algorithm comprises an artificial neural network algorithm, a deep convolutional neural network algorithm, a deep recurrent neural network, a generative adversarial network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof. In some embodiments, the machine learning algorithm is trained using a training data set comprising imaging data acquired for archived histopathological tissue samples, imaging date acquired for fresh histopathological tissue samples, or any combination thereof. In some embodiments, the training data set is continuously, periodically, or randomly updated with imaging data acquired by two or more systems that have been deployed for use at the same or different sites. In some embodiments, the two or more systems are deployed at different sites, and the training data set is continuously, periodically, or randomly updated via an internet connection. In some embodiments, the image interpretation algorithm determines an average intensity of the signal derived from the cell-associated contrast agent. In some embodiments, the image interpretation algorithm determines whether the signal for each individual cell is above a specified threshold level for contrast-positive cells. In some embodiments, the image interpretation algorithm outputs a total number of contrast-positive cells within an image, a density of contrast-positive cells within an image, a percentage of contrast-positive cells within an image, or any combination thereof. In some embodiments, the image interpretation algorithm outputs a cellularity score. In some embodiments, the images of the tissue specimen are acquired in vivo. In some embodiments, the images of the tissue specimen are acquired ex vivo. In some embodiments, the system is used during a surgical procedure to identify locations for performing a biopsy or to determine if resection is complete.

Disclosed herein are methods for detection of a cell-associated optical contrast agent in a tissue specimen, the methods comprising: a) acquiring a first high-resolution, optically-sectioned image of the tissue specimen at a first emission wavelength range that includes an emission peak of the cell-associated contrast agent, b) acquiring a second high-resolution, optically-sectioned image of the tissue specimen at a second emission wavelength range that excludes the emission peak of the cell-associated contrast agent; and c) applying a pseudo-color algorithm to the first and second images to generate a multi-color image of the tissue specimen that facilitates human interpretation. In some embodiments, the first and second high-resolution, optically-sectioned images are acquired using two-photon fluorescence microscopy, confocal fluorescence microscopy, light sheet microscopy, or structured illumination microscopy. In some embodiments, the image acquired using the first emission wavelength range is further processed by an image interpretation algorithm to identify individual cells and their locations, and outputs a total number of contrast-positive cells within the image, a density of contrast-positive cells within the image, a percentage of contrast-positive cells within the image, or any combination thereof. In some embodiments, the images of the tissue specimen are acquired in vivo. In some embodiments, the images of the tissue specimen are acquired ex vivo. In some embodiments, the method is used during a surgical procedure to identify locations for performing a biopsy or to determine if resection is complete.

Also disclosed herein are methods for guiding a surgical resection, the methods comprising; a) acquiring high-resolution, optically-sectioned images of a distribution of a cell-associated contrast agent within a tissue specimen using a first imaging modality; b) acquiring high-resolution, optically-sectioned images of tissue specimen morphology within the same optical focal plane of the tissue specimen using a second imaging modality; and c) processing the images acquired using either or both of the first and second imaging modalities using an image interpretation algorithm that identifies individual cells and determines their locations, and outputs a quantitative measure of a signal derived from the cell-associated contrast agent at cellular resolution by measuring the signal at locations corresponding to those of the individual cells in the images acquired using the first imaging modality.

Disclosed herein are methods for guiding a surgical resection, the methods comprising: a) acquiring high-resolution, optically sectioned images of a tissue specimen; and b) processing the images using an image interpretation algorithm that detects individual cells in the images and outputs a quantitative measure of a signal derived from a cell-associated contrast agent at a location of one or more individual cells.

Disclosed herein are methods for guiding a surgical resection, the methods comprising: a) acquiring a first high-resolution, optically-sectioned image of the tissue specimen at a first emission wavelength range that includes an emission peak of a cell-associated contrast agent, b) acquiring a second high-resolution, optically-sectioned image of the tissue specimen at a second emission wavelength range that excludes the emission peak of the cell-associated contrast agent; and c) applying a pseudo-color algorithm to the first and second images to generate a multi-color image of the tissue specimen that facilitates human interpretation.

For any of the methods disclosed herein, in some embodiments the images for at least one imaging modality are acquired using two-photon fluorescence microscopy, confocal fluorescence microscopy, light sheet microscopy, or structured illumination microscopy. In some embodiments, images acquired using at least a second imaging modality are acquired using stimulated Raman scattering microscopy, coherent anti-Stokes Raman scattering microscopy, confocal reflection microscopy, second harmonic generation microscopy, or third harmonic generation microscopy. In some embodiments, the tissue specimen is a brain tissue specimen, breast tissue specimen, lung tissue specimen, pancreatic tissue specimen, or prostate tissue specimen. In some embodiments, the images of the tissue specimen are acquired in vivo. In some embodiments, the images of the tissue specimen are acquired ex vivo. In some embodiments, an image interpretation algorithm used to process images acquired using a first imaging modality or a second imaging modality outputs a total number of contrast-positive cells within the image, a density of contrast-positive cells within the image, a percentage of contrast-positive cells within the image, or any combination thereof. In some embodiments, an image interpretation algorithm used to process the images acquired using a first imaging modality or a second imaging modality comprises a machine learning algorithm. In some embodiments, the machine learning algorithm comprises a supervised machine learning algorithm, an unsupervised machine learning algorithm, a semi-supervised machine learning algorithm, or any combination thereof. In some embodiments, the machine learning algorithm comprises an artificial neural network algorithm, a deep convolutional neural network algorithm, a deep recurrent neural network, a generative adversarial network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof. In some embodiments, the machine learning algorithm is trained using a training data set comprising imaging data acquired for archived histopathological tissue samples, imaging date acquired for fresh histopathological tissue samples, or any combination thereof. In some embodiments, the training data set is continuously, periodically, or randomly updated with imaging data acquired by two or more systems that have been deployed for use at the same or different sites. In some embodiments, the two or more systems are deployed at different sites, and the training data set is continuously, periodically, or randomly updated via an internet connection.

Disclosed herein are methods for guiding a surgical resection, the methods comprising; a) acquiring high-resolution, optically-sectioned images of a distribution of a cell-associated contrast agent within a tissue specimen using two photon fluorescence microscopy; b) acquiring high-resolution, optically-sectioned images of tissue specimen morphology within the same optical focal plane of the tissue specimen using stimulated Raman scattering microscopy; and c) processing the images acquired using stimulated Raman scattering using an image interpretation algorithm that identifies individual cells and determines their locations, and outputs a quantitative measure of a signal derived from the cell-associated contrast agent at cellular resolution by measuring the signal at locations corresponding to those of the individual cells in the images acquired using two photon fluorescence.

Disclosed herein are methods for guiding a surgical resection, the methods comprising: a) acquiring high-resolution, optically sectioned images of a tissue specimen using two photon fluorescence; and b) processing the images using an image interpretation algorithm that detects individual cells in the images and outputs a quantitative measure of a signal derived from a cell-associated contrast agent with cellular resolution at a location of one or more individual cells.

Disclosed herein are methods for guiding a surgical resection, the methods comprising: a) acquiring a first high-resolution, optically-sectioned two photon fluorescence image of the tissue specimen at a first emission wavelength range that includes an emission peak of a cell-associated contrast agent, b) acquiring a second high-resolution, optically-sectioned two photon fluorescence image of the tissue specimen at a second emission wavelength range that excludes the emission peak of the cell-associated contrast agent; and c) applying a pseudo-color algorithm to the first and second two photon fluorescence images to generate a multi-color image of the tissue specimen that facilitates human interpretation.

In any of the methods disclosed herein, in some embodiments images for at least one imaging modality are acquired using confocal fluorescence microscopy, light sheet microscopy, or structured illumination microscopy instead of two photon fluorescence microscopy. In some embodiments, images acquired using at least a second imaging modality are acquired using coherent anti-Stokes Raman scattering microscopy, confocal reflection microscopy, second harmonic generation microscopy, or third harmonic generation microscopy instead of stimulated Raman scattering microscopy. In some embodiments, the tissue specimen is a brain tissue specimen, breast tissue specimen, lung tissue specimen, pancreatic tissue specimen, or prostate tissue specimen. In some embodiments, images of the tissue specimen are acquired in vivo. In some embodiments, images of the tissue specimen are acquired ex vivo. In some embodiments, an image interpretation algorithm used to process images acquired using two photon fluorescence outputs a total number of contrast-positive cells within the image, a density of contrast-positive cells within the image, a percentage of contrast-positive cells within the image, or any combination thereof. In some embodiments, an image interpretation algorithm used to process the images acquired using two photon fluorescence or stimulated Raman scattering comprises a machine learning algorithm. In some embodiments, the machine learning algorithm comprises a supervised machine learning algorithm, an unsupervised machine learning algorithm, a semi-supervised machine learning algorithm, or any combination thereof. In some embodiments, the machine learning algorithm comprises an artificial neural network algorithm, a deep convolutional neural network algorithm, a deep recurrent neural network, a generative adversarial network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof. In some embodiments, the machine learning algorithm is trained using a training data set comprising imaging data acquired for archived histopathological tissue samples, imaging date acquired for fresh histopathological tissue samples, or any combination thereof. In some embodiments, the training data set is continuously, periodically, or randomly updated with imaging data acquired by two or more systems that have been deployed for use at the same or different sites. In some embodiments, the two or more systems are deployed at different sites, and the training data set is continuously, periodically, or randomly updated via an internet connection.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
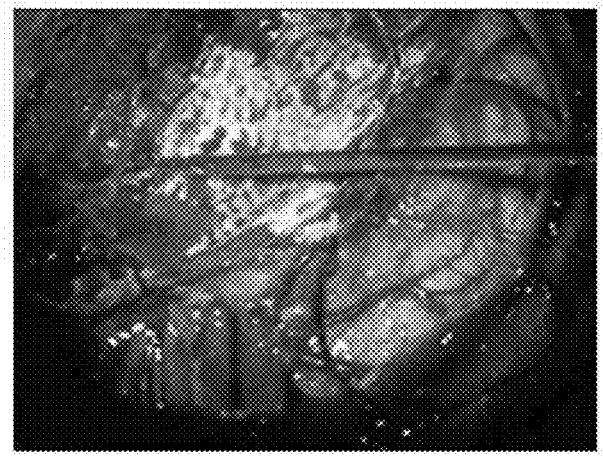
FIG. 1A provides a non-limiting example of a visible light image of brain tissue during a surgical procedure to remove a glioma.
Figure 1B:
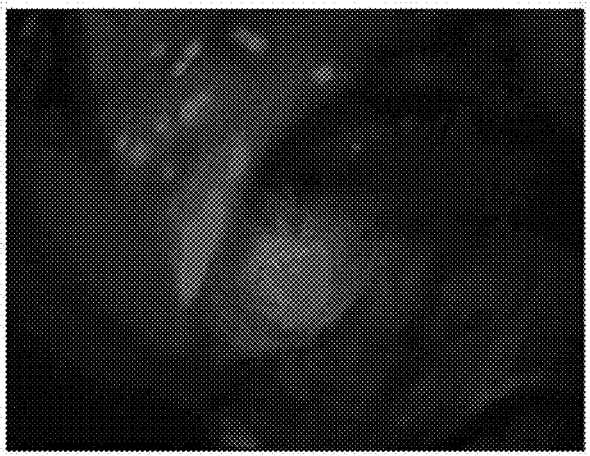
FIG. 1B provides a non-limiting example of a fluorescence image of the brain tissue illustrated in FIG. 1A, where 5-aminolevulinic acid (5-ALA) HCl has been used as a contrast agent to better visualize and guide the removal of the glioma.

Identification of neoplastic tissue at the time of surgery is critical to making adequate surgical decisions and achieving maximal safe resection in patients. In recent years, intraoperative fluorescent contrast agents such as fluorescein, 5-aminolevulinic acid (5-ALA) (NX Development Corp, Lexington, KY), BLZ-100 (Blaze Bioscience, Inc., Seattle WA), and LUM015 (Lumicell, Inc., Newton, MA), have been gaining approval and popularity. These contrast agents are typically given pre-operatively (e.g., orally or by injection) and can be visualized with traditional fluorescent surgical microscopes (e.g. the Zeiss OPMI Pentero 800 (Carl Zeiss Meditec, Inc., Dublin, CA), Leica PROvido-FL560 (Leica Microsystems Inc., Buffalo Grove, IL), or Synaptive Modus V (Synaptive Medical, Toronto, ON)). FIG. 1A provides an example of a visible light image of brain tissue treated with 5-ALA during a surgical procedure to remove a glioma. FIG. 1B shows the corresponding fluorescence image. In current practice, surgeons would resect all fluorescent tissue.

Limitations of this approach that are well known in the art include: (i) limited sensitivity at the tumor margin where the concentration of the contrast agent accumulation can be low due to the low number of tumor cells, and (ii) limited specificity due to auto-florescent background signal, non-specific staining and non-uniform delivery.

To overcome these limitations, the methods and systems disclosed herein use high-resolution optical imaging in fresh tissue specimens, either ex vivo or in vivo, to resolve the distribution of dye at cellular or sub-cellular levels in the operating room in near real-time. This approach relies on optical sectioning to be able to image fresh tissue specimens. Suitable high-resolution optical imaging techniques that may be used to visualize fluorescent contrast agents in thick tissue specimens without physically sectioning the tissue include, but are not limited to, 2-Photon Fluorescent (2P) Microscopy, Confocal Fluorescent Microcopy (CM), Light Sheet Microscopy (LSM), and Structured Illumination Microscopy (SIM). Such imaging modalities rely on optical sectioning to suppress out-of-focus signal and can have a resolution equal or better than 10 microns axially and equal or better than 5 microns laterally, i.e., sufficient resolution to image cellular and sub-cellular features. Ex vivo approaches can be preferable to achieve best image quality and sensitivity. In vivo approaches can be preferred from a clinical workflow perspective since they do not require tissue biopsy.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term 'about' a number refers to that number plus or minus 10% of that number. The term 'about' when used in the context of a range refers to that range minus 10% of its lowest value and plus 10% of its greatest value.

Tissue specimens: In some instances, the disclosed systems and methods may be used for characterization of any of a variety of tissue specimens known to those of skill in the art. Examples include, but are not limited to, connective tissue, epithelial tissue, muscular tissue, lung tissue, pancreatic tissue, breast tissue, kidney tissue, liver tissue, prostate tissue, thyroid tissue, and nervous tissue specimens. In some instances, the tissue specimen may be derived from any organ or component of a plant or animal. In some instances, the tissue specimen may be derived from any organ or other component of the human body including, but not limited to, the brain, heart, lungs, kidneys, liver, stomach, bladder, intestines, skeletal muscle, smooth muscle, breast, prostate, pancreas, thyroid, etc. In some instances, the tissue specimen may comprise a specimen collected from a patient exhibiting an abnormality or disease, e.g., a tumor or a cancer (e.g., sarcomas, carcinomas, gliomas, etc.).

Tissue specimen collection: Procedures for obtaining tissue samples from an individual are well known in the art. For example, procedures for drawing and processing tissue samples such as from a needle aspiration biopsy, core needle biopsy or surgical biopsy are well-known and may be employed to obtain a tissue specimen for analysis using the disclosed systems and methods. Typically, for collection of such a tissue sample, a thin hollow needle is inserted into a mass such as a tumor mass or the mass is exposed surgically for sampling of the tissue that, after being stained, will be examined under a microscope.

Contrast agents: In some instances, the disclosed methods and systems comprise the use of contrast agents for enhancing and/or differentiating the appearance of neoplastic tissue, benign tissue, and malignant tissue in images of tissue specimens. As used herein, the terms "contrast agents" and "optical contrast agents" are used interchangeably. As used herein, the terms "fluorescent contrast agent" and "phosphorescent contrast agent" refer to subsets of optical contrast agents that emit fluorescence or phosphorescence respectively when properly excited. Examples of fluorescent contrast agents include, but are not limited to, 5-aminolevulinic acid hydrochloride (5-ALA), BLZ-100, and LUM015. In some instances, the disclosed methods and systems comprise the measurement of a signal derived from a contrast agent, e.g., a cell-associated contrast agent, which may be a signal generated by the contrast agent itself or by a metabolized or processed form thereof.

5-ALA is a compound that is metabolized intracellularly to form the fluorescent protoporphyrin IX (PPIX) molecule. The exogenous application of 5-ALA leads to a highly selective accumulation of PPIX in tumor cells and epithelial tissues. PPIX is excited with blue light (excitation maxima at about 405 nm and 442 nm) and emits in the red (emission maxima at about 630 nm and 690 nm) (see, e.g., Wang, et al. (2017), "Enhancement of 5-aminolevulinic acid-based fluorescence detection of side population-defined glioma stem cells by iron chelation", Nature Scientific Reports 7:42070).

BLZ-100 comprises the tumor ligand chlorotoxin (CTX) conjugated to indocyanine green (ICG), and has shown potential as a targeted contrast agent for brain tumors, etc. (see, e.g., Butte, et al. (2014), "Near-infrared imaging of brain tumors using the Tumor Paint BLZ-100 to achieve near-complete resection of brain tumors", Neurosurg Focus 36 (2): E1). BLZ-100 is typically excited in the near-infrared at about 780 nm (the broad ICG absorption peak being centered at approximately 800 nm), with the broad fluorescence emission spectrum (having an emission maximum at approximately 810 nm-830 nm) nearly overlapping the absorption spectrum.

LUM015, is a protease-activated imaging agent comprising a commercially-available fluorescence quencher molecule (QSY® 21) attached through a Gly-Gly-Lys-Arg (GGRK) peptide to a 20-kD polyethylene glycol (PEG) and a Cyanine dye 5 (Cy5) fluorophore. The intact molecule is optically inactive, but upon proteolytic cleavage by cathepsins K, L, or S, etc., the quencher is released to create optically active fragments (see, e.g., Whitley, et al. (2016) "A mouse-human phase 1 co-clinical trial of a protease-activated fluorescent probe for imaging cancer", Science Translational Medicine 8(320) pp. 320ra4). The Cy5-labeled fragment has a fluorescence excitation peak at about 650 nm and an emission peak at 670 nm.

Contrast agents may be applied to tissue specimens for ex vivo imaging using any of a variety of techniques known to those of skill in the art, e.g., by applying a solution of the contrast agent to a tissue section as a staining reagent. Contrast agents may be administered to subjects, e.g., patients, for in vivo imaging by any of a variety of techniques known to those of skill in the art including, but not limited to, orally, by intravenous injection, etc., where the choice of technique may be dependent on the specific contrast agent.

For any of the imaging methods and systems disclosed herein, the tissue specimen may in some instances be stained with one or more optical contrast agents. For example, in some instances, the tissue specimen may be stained with one, two, three, four, or more than four different optical contrast agents.

As noted, in some instances, the one or more optical contrast agents may comprise fluorescent contrast agents that emit fluorescence signals. In some instances, the one or more optical contrast agents may comprise phosphorescent contrast agents that emit phosphorescence signals. In some instances, the one or more optical contrast agents may comprise contrast agents that specifically associate with cells in the tissue specimen. In some instances, the one or more optical contrast agents may comprise contrast agents that specifically associate with one or more specific types of cells (e.g., "targeted" cells). In some instances, the one or more optical contrast agents may comprise, e.g., an antibody conjugated to a fluorophore, a quantum dot, a nanoparticle, or a phosphor. In some instances, the cell-associated contrast agent may comprise a fluorogenic enzyme substrate designed to target cell types that express a specific enzyme.

Intraoperative use: In some instances, the disclosed methods and systems may be used intraoperatively, e.g., to guide a surgical procedure, to identify locations for performing a biopsy, or to determine if resection is complete. In some instances, the disclosed systems may be deployed in an operating room environment to provide real-time or near real-time in vivo imaging capability and guidance to a surgeon performing a surgical procedure.

High-resolution, optically-sectioned fluorescence and related imaging microscopies: High-resolution optical imaging techniques suitable for visualizing the distribution of fluorescent contrast agents in thick tissue specimens without physically sectioning the tissue include, but are not limited to, two-photon fluorescence (2P or TPF) microscopy, three-photon fluoresced (3P) microscopy, confocal fluorescence microscopy (CFM), light sheet fluorescence microscopy (LSFM), and structured illumination microscopy (SIM). In general, these techniques rely on, e.g., confocal optics and/or the tight focusing of excitation laser beams required to stimulate two photon fluorescence and other optical processes for achieving small depth of field that enables optically-sectioned imaging of thick tissue specimens. Some of these techniques are compatible with other optical emission modes, e.g., phosphorescence, as well as fluorescence.

Two photon fluorescence microscopy: Two photon (2P) fluorescence microscopy is a fluorescence imaging technique in which the absorption of two excitation photons by a dye molecule excites an electronic transition that yields emission of a single emitted photon having a wavelength that is shorter than that of the excitation light. Two-photon fluorescence microscopy typically uses near-infrared (NIR) excitation light, which minimizes scattering in tissue samples. The multiphoton absorption process also suppresses background signal (due to the nonlinear interaction with the tissue specimen, which confines the excitation of fluorescence primarily to the focal plane) and contributes to increased tissue penetration depth (up to about one millimeter in thickness). In addition to deeper tissue penetration, two-photon excitation has the advantages of efficient light detection and reduced photobleaching (see, e.g., Denk, et al., (1990), "Two-Photon Laser Scanning Fluorescence Microscopy", Science 248:4951: 73-76).

Confocal fluorescence microscopy: Confocal fluorescence microscopy (CFM) is an imaging technique that provides three-dimensional optical resolution by actively suppressing laser-induced fluorescence signals coming from out-of-focus planes. This is typically achieved by using a pinhole in front of the detector such that light originating from an in-focus plane is imaged by the microscope objective and passes the pinhole, whereas light coming from out-of-focus planes is largely blocked by the pinhole (see, e.g., Combs (2010), "Fluorescence Microscopy: A Concise Guide to Current Imaging Methods", Curr. Protocols in Neurosci. 50(1):2.1.1-2.1.14; Sanai, et al. (2011), "Intraoperative confocal microscopy in the visualization of 5-aminolevulinic acid fluorescence in low-grade gliomas", J. Neurosurg. 115(4):740-748; Liu, et al. (2014), "Trends in Fluorescence Image-guided Surgery for Gliomas", Neurosurgery 75(1): 61-71).

Light sheet fluorescence microscopy: Light sheet fluorescence microscopy (LSFM) uses a plane of light (typically produced by expanding a laser beam to fill a cylindrical lens and/or slit aperture) to optically section and view tissues with subcellular resolution and allows for imaging deep within transparent tissues. Because tissues are exposed to a thin sheet of light, photobleaching and phototoxicity are minimized compared to wide-field fluorescence, confocal, or multiphoton microscopy techniques (see, e.g., Santi (2011), "Light Sheet Fluorescence Microscopy: A Review", J. of Histochem. & Cytochem. 59(2):129-138; Meza, et al. (2015), "Comparing high-resolution microscopy techniques for potential intraoperative use in guiding low-grade glioma resections", Lasers in Surg. And Med. 47(4):289-295; Glaser, et al. (2017), "Light-sheet microscopy for slide-free non-destructive pathology of large clinical specimens", Nat Biomed Eng. 1(7):0084).

Structured illumination fluorescence microscopy: Structured illumination fluorescence microscopy (SIM) is a method of obtaining optical sectioning in conventional wide-field microscopes by projecting a single-spatial frequency grid pattern of excitation light onto the sample. Images taken at, for example, three spatial positions of the grid are processed to produce optically sectioned images that are similar to those obtained using confocal microscopes (see, e.g., Neil, et al. (1997), "Method of Obtaining Optical Sectioning By Using Structured Light In A Conventional Microscope", Optics Lett. 22(24):1905-1907).

High-resolution, optically-sectioned non-fluorescence imaging microscopies: High-resolution optically-sectioned non-fluorescence imaging microscopies suitable for imaging tissue morphology include but are not limited to: stimulated Raman scattering (SRS) microscopy, coherent anti-Stokes Raman scattering (CARS) microscopy, confocal reflection (CR) microscopy, second harmonic generation (SHG) microscopy, and third harmonic generation (THG) microscopy. In general, these techniques rely on the tight focusing of excitation laser beams required to stimulate SRS, CARS, SHG or THG scattering or emission to achieve the small depth of field that enables optically-sectioned imaging of thick tissue specimens.

Stimulated Raman scattering (SRS) microscopy: Stimulated Raman scattering (SRS) microscopy is an imaging technique that provides rapid, label-free, high-resolution microscopic imaging of unprocessed tissue specimens. SRS microscopy requires two laser pulse trains that are temporally overlapped such that the temporal mismatch is less than the pulse duration (e.g., less than 100 fsec), and spatially overlapped by less than the focal spot size (e.g., less than 100 nm). The imaging of the stimulated Raman scattering induced in the sample by the pair of spatially and temporally synchronized laser pulse trains enables mapping of distinct molecule components within the tissue specimen based on image acquisition at the vibrational frequencies (or wavenumbers) corresponding to, for example, the $CH_2$-vibration of lipid molecules (2,850 $cm^{-1}$) or the $CH_3$-vibration of protein and nucleic acid molecules (2,930 $cm^{-1}$) (see, e.g., Freudiger, et al. (2008), "Label-Free Biomedical Imaging with High Sensitivity by Stimulated Raman Scattering Microscopy", Science 322:1857-186; and Orringer, et al. (2017), "Rapid Intraoperative Histology of Unprocessed Surgical Specimens via Fibre-Laser-Based Stimulated Raman Scattering Microscopy", Nature Biomed. Eng. 1:0027).

Coherent anti-Stokes Raman scattering (CARS) microscopy: Coherent anti-Stokes Raman scattering (CARS) microscopy is a label-free imaging technique which forms images of structure in samples, e.g., tissue specimens, by displaying the characteristic intrinsic vibrational contrast arising from the molecular components of the sample (see, e.g., Camp, et al. (2014), "High-speed coherent Raman fingerprint imaging of biological tissues", Nat. Photon. 8, 627-634; and Evans, et al. (2007), "Chemically-selective imaging of brain structures with CARS microscopy", Opt. Express. 15, 12076-12087). The technique uses two high-powered lasers to irradiate the sample, where the frequency of the first laser is typically held constant and the frequency of the second is tuned so that the frequency difference between the two lasers is equal to the frequency of a Raman-active mode of interest. CARS is orders of magnitude stronger than typical Raman scattering.

Confocal reflection (CR) microscopy: Confocal reflection microscopy, performed using a confocal microscope to take advantage of the optical sectioning capabilities of the confocal optics while operating in reflectance mode rather than fluorescence mode, may be used to image unstained tissues or tissues labeled with probes that reflect light. Near-infrared confocal laser scanning microscopy, for example, uses a relatively low-power laser beam focused tightly on a specific point in the tissue. Only light that is back-scattered from the focal plane is detected, with contrast caused by native variations in the refractive index of tissue microstructures. (see, e.g., Gonzalez, et al. (2002), "Real-time, in vivo confocal reflectance microscopy of basal cell carcinoma", J. Am. Acad. Dermatol. 47(6):869-874).

Second harmonic generation (SHG) microscopy: SHG microscopy is a non-fluorescent multiphoton imaging technique that utilizes second harmonic generation, a nonlinear optical process in which two excitation photons of a given wavelength interact with a material comprising a non-centrosymmetric structure and are "converted" to form an emitted photon that has half the wavelength of the excitation light. A laser source focused to a tight focal plane spot is typically required for exciting second harmonic light, and imaging the light thus generated enables the acquisition of high-resolution, optically sectioned images of biological tissues comprising, e.g., collagen fibers (see, e.g., Bueno, et al. (2016), "Second Harmonic Generation Microscopy: A Tool for Quantitative Analysis of Tissues", Chapter 5 in *Microscopy and Analysis*, Stefan Stanciu, Ed., InTech Open).

Third harmonic generation (THG) microscopy: THG microscopy is also a non-fluorescent multiphoton imaging technique that combines the advantages of label-free imaging with restriction of signal generation to the focal spot of the scanning laser. Third harmonic generation is a process in which three excitation photons interact with matter to produce a single emitted photon having a wavelength that is one-third that of the excitation light. It allows high resolution optically sectioned imaging of refraction index mismatches in biological tissues (see, e.g., Dietzel (2014), "Third harmonic generation microscopy", Wiley Analytical Science, Imaging and Microscopy, Nov. 11, 2014).

Multispectral and/or multimodal imaging methods and systems for qualitative and quantitative detection of cell-associated contrast agents: The disclosed imaging methods and systems comprise the use of novel combinations of multispectral and/or multimodal in vivo or ex vivo imaging to detect the distribution of optical contrast agents, e.g. cell-associated fluorescent contrast agents, within tissue specimens and provide qualitative and/or quantitative measurements of signals arising from said optical contrast agents (see, e.g., Yue, et al. (2011), "Multimodal nonlinear optical microscopy", Laser and Photonics Review 5(4):496-512 for a review of conventional multimodal imaging techniques). The disclosed multispectral and/or multimodal imaging methods and systems provide more accurate quantitative measures of signal arising from optical contrast agents by using image interpretation algorithms to correct for background signals (e.g., auto-fluorescence background and/or highly-fluorescent granules) and resolve the measured signals at the cellular or sub-cellular level. The unexpected ability to resolve and measure signals arising from cell-associated optical contrast agents at the cellular or sub-cellular level (due in part to the improved detection sensitivity achieved through the use of novel dual wavelength fiber laser systems (as described in U.S. Pat. Nos. 8,792,156; 9,104,030; and 9,634,454) and improved image contrast) leads to significant improvements in quantitation. In some instances, the disclosed multispectral and/or multimodal imaging methods and systems allow one to overlay images, e.g., a two-photon fluorescence image and a stimulated Raman scattering image, to provide enhanced contrast and/or to generate pseudo-color images that facilitate direct human interpretation.

In a first aspect, the disclosed imaging methods (and systems configured to perform said methods) may comprise the use of a high resolution, optically-sectioned microscopy technique including, but not limited to, two-photon microscopy, confocal fluorescence microscopy, light sheet microscopy, or structured illumination microscopy to acquire images at one, two, or more than two detection wavelengths (or within one, two, or more than two detection wavelength ranges) using excitation light at one, two, or more than two excitation wavelengths (or within one, two, or more than two excitation wavelength ranges). The disclosed imaging methods (and systems configured to perform said methods) subsequently apply an image interpretation algorithm to detect contrast-positive cells based on size, shape, pattern or intensity and exclude background signals, e.g., highly-fluorescent granules based on size, shape, pattern or intensity, to provide a quantitative measure of the signal arising from a cell-associated contrast agent, where the quantitative measure of the signal is resolved at the cellular level. A specific example of this embodiment will be described in more detail below. In some instances, the image interpretation algorithm may provide a qualitative and/or quantitative measure derived from the signal(s) associated with one or more optical contrast agents. For example, in some instances, the image interpretation algorithm may provide a "cellularity score", e.g., a determination of the number of cells (or cell nuclei). Results can also be presented as a density per unit area of the imaged tissue specimen. In some instances, the image interpretation algorithm may provide an average signal derived from the cell-associated contrast agent. In some instances, the image interpretation algorithm may provide an average signal for the contrast-positive cells after subtracting out a background signal averaged over the entire image. In some instances, the image interpretation algorithm may provide the number of cells for which the signal is greater than a specified signal threshold that defines a contrast-positive cell. In some instances, the image interpretation algorithm may provide the percentage of total cells in the image that are contrast-positive. In some instances, the disclosed methods and systems may be used during a surgical procedure to identify locations for performing a biopsy or to determine if resection is complete.

In a second aspect, the disclosed methods (and systems configured to perform said methods) combine the cellular imaging of one or more contrast agents using a first optical-sectioning high-resolution microscopy (e.g. 2P, CFM, LSM, or SIM), i.e., a first imaging modality, with a second optical-sectioning high-resolution microscopy (e.g., SRS, CARS, CR, SHG, or THG), i.e., a second imaging modality, used to image the tissue morphology in the same optical focal plane of the tissue specimen independently of the presence of the one or more contrast agents. The instrument then processes the images using an image interpretation algorithm to provide the location and/or area of one or more individual cells based on the image(s) acquired using the second imaging modality, and provides a quantitative measure of the signal arising from the one or more contrast agents in the tissue specimen based on the image(s) acquired using the first modality at the location(s) and/or areas corresponding to the one or more cell(s) such that the quantitative measure of signal is resolved at the cellular level. A specific example of this embodiment will be described in more detail below. In some instances, the instrument processes the images using an image interpretation algorithm to provide the location and/or size of one or more individual cells based on the image(s) acquired using the first imaging modality, and provides a quantitative measure of the signal arising from the one or more contrast agents in the tissue specimen based on the image(s) acquired using the first modality at the location(s) and/or areas corresponding to the one or more cell(s). In some instances, the quantitative measure may be derived from the signal arising from the one or more contrast agents at the location(s) and/or areas corresponding to the one or more cell(s), or may be derived from a signal derived from the images acquired using the second imaging modality, e.g., an SRS signal, at the location(s) and/or areas corresponding to the one or more cell(s), or may be derived from a combination of both signals arising from the one or more contrast agents and signals derived from the imaged acquired using the second imaging modality at the location(s) and/or areas corresponding to the one or more cell(s). In some instances, the image interpretation algorithm may provide a qualitative and/or quantitative measure derived from the signal(s) associated with one or more optical contrast agents. For example, in some instances, the image interpretation algorithm may provide: (i) a "cellularity score" as discussed above, (ii) an average signal derived from the cell-associated contrast agent, (iii) an average signal for the contrast-positive cells after subtracting out a background signal averaged over the entire image, (iv) the number of cells for which the signal is greater than a specified signal threshold that defines a contrast-positive cell, (v) the percentage of total cells in the image that are contrast-positive, or any combination thereof. In some instances, the disclosed methods and systems may be used during a surgical procedure to identify locations for performing a biopsy or to determine if resection is complete.

In a third aspect, the imaging system may be, e.g., a multi-channel imaging microscope that simultaneously acquires a first image at the emission wavelength of the contrast agent and a second image outside the emission wavelength of the contrast agent, and then provides the multi-channel emission signals to an image interpretation algorithm that detects cells in the first image and suppresses non-specific background signal (e.g., auto-fluorescent background or highly-fluorescent granules) based on the measured spectral characteristics (e.g., by ratioing or thresholding the first image using the signal data acquired in the second image, (e.g., at the locations corresponding to one or more cells detected in the first image), or otherwise correcting signals measured in the first image by a background value determined from the second image). In some instances, it is possible to create multi-color images based on application of a pseudo-color algorithm to the multi-channel image data (e.g., by assigning a contrast agent-associated signal to red and a background signal to green) to simplify human interpretation of the image. The latter approach may avoid the need for computer-assisted interpretation algorithms. An example of this embodiment of the disclosed imaging methods and systems will be described in more detail below.

Image acquisition parameters: For any of the imaging methods and systems disclosed herein, images of tissue specimens may be acquired using a variety of image acquisition parameter settings including, but not limited to, the effective image resolution, the number of excitation wavelengths used, the number of emission wavelengths at which images are acquired, the number of images acquired over a specified period of time, the number of different imaging modalities used to acquire images that are then processed and/or combined to: (i) create multi-color or enhanced contrast images that facilitate image interpretation and the identification of, e.g., neoplastic tissue, if present in the tissue specimen, and/or (ii) to generate quantitative measures based on the signal(s) derived from one or more cell-associated contrast agents and/or signals derived from a second imaging modality, e.g. a non-fluorescence imaging modality such as SRS.

In some instances, the disclosed imaging systems may comprise laser scanning systems, e.g. systems in which an image is acquired in two dimensions by scanning or rastering a laser spot across the optical focal plane of the imaging system, and emitted or scattered light, e.g. two photon fluorescence or stimulated Raman scattered light is directed through the optical system to one or more photodetectors, e.g., photomultipliers, avalanche photodiodes, solid-state near-infrared detectors, and the like. In some instances, if the imaging system comprises two or more photodetectors, the two or more detectors may be of the same type or may be of different types. In some instances, two or more detectors of different types may differ in terms of size (diameter or cross-sectional area), integration time, signal-to-noise ratio, sensitivity, etc.

In some instances, the disclosed imaging systems may comprise laser scanning systems that utilize one or more image sensors or cameras. For example, in some instances, the disclosed imaging systems may comprise one, two, three, four, or more than four image sensors or cameras. In some instances, e.g., if the imaging system comprises two or more image sensors or cameras, the image sensors or cameras may be the same or may differ in terms of pixel size, pixel count, dark current, signal-to-noise ratio, detection sensitivity, etc. The images thus acquired by the two or more image sensors or cameras may thus have different image resolutions. In some instances, the one or more image sensors may have a pixel count of about 0.5 megapixel, 1 megapixel, 2 megapixels, 4 megapixels, 6 megapixels, 8 megapixels, 10 megapixels, 20 megapixels, 50 megapixels, 80 megapixels, 100 megapixels, 200 megapixels, 500 megapixels, or 1000 megapixels (or any pixel count within the range spanned by these values). In some instances, the size of the pixels within a given image sensor may be about 20 µm, 10 µm, 5 µm, 3.5 µm, 2 µm, 1 µm, 0.5 µm, or 0.1 µm (or any pixel size within the range spanned by these values). In some instances, the one or more image sensors or cameras may be configured to bin groups of individual pixels to vary the effective resolution of the images thus acquired.

In some instances, the disclosed imaging systems (either scanning systems or image sensor-based systems) may be configured to acquire a single image for each of one or more specified excitation wavelengths, emission wavelengths, and/or imaging modalities. In some instances, the disclosed systems may be configured to acquire 2, 3, 4, 5, 6, 7, 8, 9, 10, 20, 30, 40, 50, 60, 70, 80, 90, 100, or more than 100 images (or any number of images within this range) for each of one or more specified excitation wavelengths, emission wavelengths, and/or imaging modalities. In some instances, the discloses systems may be configured to acquire video data for each of one or more specified excitation wavelengths, emission wavelengths, and/or imaging modalities.

In some instances, the disclosed imaging systems may be configured to acquire one or more images within a specified time period for each of one or more specified excitation wavelengths, emission wavelengths, and/or imaging modalities. For example, in some instances, the disclosed systems may be configured to acquire one or more images every 0.1 msec, 1 msec, 10 msec, 20 msec, 30 msec, 40 msec, 50 msec, 60 msec, 70 msec, 80 msec, 90 msec, 100 msec, 200 msec, 300 msec, 400 msec, 500 msec, 600 msec, 700 msec, 800 msec, 900 msec, 1 sec, 2, sec, 3 sec, 4 sec, 5 sec, 6 sec, 7 sec, 8 sec, 9 sec, 10 sec, 20 sec, 30 sec, 40 sec, 50 sec, 1 min, 2 min, 3 min, 4 min, 5 min, 6 min, 7 min, 8 min, 9 min, 10 min, 20 min, 30 min, 40 min, 50 min, 1 hour, 2 hours, 3 hours, 4 hours, 5 hours, 6 hours, 7 hours, 8 hours, 9 hours, 10 hours (or any time period within this range) for each of one or more specified excitation wavelengths, emission wavelengths, and/or imaging modalities. In some instances, the disclosed systems may be configured to acquire video data for each of one or more specified excitation wavelengths, emission wavelengths, and/or imaging modalities.

In some instances, the disclosed imaging systems may be configured to acquire images using an exposure time (or integration time, or image capture time) of about 1 msec, 5 msec, 10 msec, 25 msec, 50 msec, 75 msec, 100 msec, 250 msec, 500 msec, 750 msec, 1 sec, 2 sec, 3 sec, 4 sec, 5 sec, 6 sec, 7, sec, 8 sec, 9 sec, 10 sec, 20 sec, 30 sec, 40 sec, 50 sec, 60 sec, or more than 60 sec (or any exposure time, image capture time, or integration time within the range spanned by these values).

In some instances, including but not limited to those in which two-photon fluorescence imaging is utilized, images may be acquired using one, two, three, four, or more than four different excitation wavelengths (or wavelength ranges). In some instances, images may be acquired using excitation light of about 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, 900 nm, 920 nm, 940 nm, 960 nm, 980 nm, 1000 nm, 1020 nm, 1040 nm, 1060 nm, 1080 nm, 1100 nm, 1120 nm, 1140 nm, 1160 nm, 1180 nm, or 1200 nm, where the excitation wavelength(s) used will typically be selected based on the choice of optical contrast agents used to stain the tissue specimen. In some instances, light at one, two, three, four, or more than four excitation wavelengths may be provided by one, two, three, four, or more than four lasers or other light sources. In some instances, the excitation wavelengths (or wavelength ranges) may be selected using optical glass filters, bandpass filters, interference filters, long-pass filters, short-pass filters, dichroic reflectors, monochromators, or any combination thereof.

In some instances, including but not limited to those in which two-photon fluorescence imaging is utilized, images may be acquired for one, two, three, four, or more than four different emission (or detection) wavelengths (or emission (or detection) wavelength ranges). In some instances, images may be acquired for light emitted at about 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, 900 nm, 920 nm, 940 nm, 960 nm, 980 nm, 1000 nm, 1020 nm, 1040 nm, 1060 nm, 1080 nm, 1100 nm, 1120 nm, 1140 nm, 1160 nm, 1180 nm, or 1200 nm, where the detection (emission) wavelength(s) used will typically be selected based on the choice of optical contrast agents used to stain the tissue specimen. In some instances, the emission (or detection) wavelengths (or emission (or detection) wavelength ranges) may be selected using optical glass filters, bandpass filters, interference filters, long-pass filters, short-pass filters, dichroic reflectors, monochromators, or any combination thereof.

In some instances, images may be acquired using excitation and/or emission (detection) wavelength ranges comprising a bandwidth of about 10 nm, 20 nm, 30 nm, 40 nm, 50 nm, 60 nm, 70 nm, 80 nm, 90 nm, 100 nm, or more than 100 nm. In some instances, the bandpass for excitation and/or emission wavelength ranges may be selected using optical glass filters, bandpass filters, interference filters, long-pass filters, short-pass filters, dichroic reflectors, monochromators, or any combination thereof.

In some instances, the images acquired by the disclosed imaging systems may have a lateral resolution of less than 20 µm, 15 µm, 10 µm, 9 µm, 8 µm, 7 µm, 6 µm, 5 µm, 4 µm, 3 µm, 2 µm, 1 µm, 0.5 µm, or 0.25 µm. In some instances, the lateral resolution of the disclosed imaging systems may be limited by the size of a focused laser spot.

In some instances, the images acquired by the disclosed imaging systems may have an axial resolution of less than 50 µm, 20 µm, 15 µm, 10 µm, 9 µm, 8 µm, 7 µm, 6 µm, 5 µm, 4 µm, 3 µm, 2 µm, 1 µm, or 0.5 µm. In some instances, the axial resolution of the disclosed imaging systems may be limited by the size of a focused laser spot. In some instances, the axial resolution of the disclosed imaging systems may be limited by the diameter of a pinhole aperture in a confocal optical system.

In some instances, the disclosed imaging systems are configured to acquire images of the tissue specimen at the same focal plane for two or more imaging modalities. In some instances, the focal planes for two different imaging modalities may be considered the "same" (or coplanar) if they are offset from each other by less than 10 µm, less than 9 µm, less than 8 µm, less than 7 µm, less than 6 µm, less than 5 µm, less than 4 µm, less than 3 µm, less than 2 µm, less than 1 µm, less than 0.5 µm, or less than 0.25 µm.

In some instances, including but not limited to those for which SRS imaging is utilized, images may be acquired at one or more selected wavenumbers (or wavenumber spectral ranges) that correspond to the Raman shifts for different chemical groups. In some instances, images may be acquired at one, two, three, four, or more than four different wavenumbers (or wavenumber spectral ranges). Examples of wavenumber ranges that correspond to the Raman shifts for specific chemical groups include, but are not limited to, those listed in Table 1.

TABLE 1

Examples of Raman Shifts Data for Different Chemical Groups

| Approximate Wavenumber Range | Group |
| --- | --- |
| 1610-1740 | Carboxylic acid |
| 1625-1680 | C=C |
| 1630-1665 | C=N |
| 1710-1725 | Aldehyde |
| 1710-1745 | Ester |
| 1730-1750 | Aliphatic ester |
| 2530-2610 | Thiol |
| 2680-2740 | Aldehyde |
| 2750-2800 | N—CH3 |
| 2770-2830 | CH2 |
| 2780-2830 | Aldehyde |
| 2790-2850 | O—CH3 |
| 2810-2960 | C—CH3 |
| 2870-3100 | Aromatic C—H |
| 2880-3530 | OH |
| 2900-2940 | CH2 |
| 2980-3020 | CH=CH |
| 3010-3080 | =CH2 |
| 3150-3480 | Amide |
| 3150-3480 | Amine |
| 3200-3400 | Phenol |
| 3210-3250 | Alcohol |
| 3250-3300 | Alkyne |

In some instances, including but not limited to those for which SRS imaging is utilized, images may be acquired in a spectral range spanning from about 100 $cm^{-1}$ to about 3000 $cm^{-1}$. In some instances, images may be acquired in a spectral range that spans at least 100 $cm^{-1}$, at least 125 $cm^{-1}$, at least 150 $cm^{-1}$, at least 200 $cm^{-1}$, at least 250 $cm^{-1}$, at least 300 $cm^{-1}$, at least 350 $cm^{-1}$, at least 400 $cm^{-1}$, at least 450 $cm^{-1}$, at least 500 $cm^{-1}$, at least 550 $cm^{-1}$, at least 600 $cm^{-1}$, at least 650 $cm^{-1}$, at least 700 $cm^{-1}$, at least 750 $cm^{-1}$, at least 800 $cm^{-1}$, at least 900 $cm^{-1}$, at least 1000 $cm^{-1}$, at least 1100 cm$^{-1}$, at least 1200 cm$^{-1}$, at least 1300 cm$^{-1}$, at least 1400 cm$^{-1}$, at least 1500 cm$^{-1}$, at least 1750 cm$^{-1}$, at least 2000 cm$^{-1}$, at least 2250 cm$^{-1}$, at least 2500 cm$^{-1}$, at least 2750 cm$^{-1}$, or at least 3000 cm$^{-1}$. In some instances, images may be acquired in a spectral range that spans at most 3000 cm$^{-1}$, at most 2750 cm$^{-1}$, at most 2500 cm$^{-1}$, at most 2250 cm$^{-1}$, at most 2000 cm$^{-1}$, at most 1750 cm$^{-1}$, at most 1500 cm$^{-1}$, at most 1400 cm$^{-1}$, at most 1300 cm$^{-1}$, at most 1200 cm$^{-1}$, at most 1100 cm$^{-1}$, at most 1000 cm$^{-1}$, at most 900 cm$^{-1}$, at most at 800 cm$^{-1}$, at most 750 cm$^{-1}$, at most 700 cm$^{-1}$, at most 650 cm$^{-1}$, at most 600 cm$^{-1}$, at most 550 cm$^{-1}$, at most 500 cm$^{-1}$, at most 450 cm$^{-1}$, at most 400 cm$^{-1}$, at most 350 cm$^{-1}$, at most 300 cm$^{-1}$, at most 250 cm$^{-1}$, at most 200 cm$^{-1}$, or at most 150 cm$^{-1}$. In some instances, images may be acquired using a spectral range that spans, e.g., about 250 cm$^{-1}$. Those of skill in the art will appreciate that images may be acquired in a spectral range that falls anywhere within any range bounded by any of these values (e.g., from a range of about 200 cm$^{-1}$ to a range of about 760 cm$^{-1}$).

Multispectral and/or multimodal imaging system components: For any of the embodiments described herein, the disclosed imaging systems may comprise one or more excitation light sources (e.g., solid-state lasers, fiber lasers, etc.), one or more image sensors or photodetectors (e.g., photomultipliers, avalanche photodiodes, solid-state near-infrared detectors, charge-coupled device (CCD) sensors or cameras, CMOS image sensors or cameras, etc.), one or more scanning mirrors or translation stages, and additional optical components, e.g. objective lenses, additional lenses used for collimating, focusing, and/or imaging excitation and/or emission light beams, mirrors, prisms, optical filters, colored glass filters, narrowband interference filters, broadband interference filters, dichroic reflectors, diffraction gratings, monochromators, apertures, optical fibers, optical waveguides, and the like, or any combination thereof. In some instances, the disclosed imaging systems may comprise one, two, three, four, or more than four lasers that provide excitation light at one, two, three, four, or more than four excitation wavelengths. In some instances, excitation light at one, two, three, four, or more than four excitation wavelengths may be delivered to the optical focal plane through the objective lens used for imaging the tissue specimen, e.g., by using an appropriate combination of mirrors, dichroic reflectors, or beam-splitters. In some instance, excitation light at one, two, three, four, or more than four excitation wavelengths may be delivered to the optical focal plane using an optical path that does not include the objective lens used for imaging the specimen. In some instances, the disclosed imaging systems are configured to acquire images for two or more imaging modalities from the same optical plane (or focal plane) within the tissue specimen. In some instances, the disclosed imaging systems are configured to acquire images for two or more imaging modalities for the same field-of-view within the tissue specimen. In some instances, the disclosed imaging systems may comprise one or more processors or computers, as will be discussed in more detail below. In some instances, an instrument designed to acquire images using a first imaging modality, e.g., SRS imaging or 2P imaging, may be modified to enable simultaneous or serial acquisition of images using a second imaging modality, e.g., 2P imaging or SRS imaging, respectively.

A non-limiting example of a stimulated Raman scattering (SRS) imaging system has been described by Orringer, et al. (2017), "Rapid intraoperative histology of unprocessed surgical specimens via fibre-laser-based stimulated Raman scattering microscopy", Nature Biomed. Eng. 1:0027). The fully-integrated SRS imaging system comprised five major components: (1) a fiber-coupled microscope with a motorized stage; (2) a dual-wavelength fiber-laser module; (3) a laser control module; (4) a microscope control module; and (5) a computer for image acquisition, display, and processing. The design of the dual-wavelength fiber-laser exploited the fact that the difference frequency of the two major fiber gain media, erbium and ytterbium, overlaps with the high wavenumber region of Raman spectra. The two synchronized narrow-band laser pulse trains required for SRS imaging were generated by narrow-band filtering of a broad-band super-continuum derived from a single fiber-oscillator and, subsequently, amplification in the respective gain medium. The development of an all-fiber system based on polarization-maintaining components greatly improved laser stability over previous non-polarization-maintaining implementations. To enable high-speed diagnostic-quality imaging (e.g., 1 megapixel images acquired in about 2 seconds per wavelength) with a signal-to-noise ratio comparable to what can be achieved with solid-state lasers, the laser output power was scaled to approximately 120 mW for a fixed wavelength 790 nm pump beam and approximately 150 mW for a tunable Stokes beam over the entire tuning range from 1,010 to 1,040 nm at 40 MHz laser pulse repetition rate and 2 picosecond transform-limited laser pulse duration. Custom laser controller electronics were developed to tightly control the operational settings of the laser system using a microcontroller. A noise-cancellation scheme based on auto-balanced detection, in which a portion of the laser beam is sampled to provide a measure of the laser noise that can then be subtracted in real time, was used to further improve image quality. In some instances, a system such as the described SRS imaging system may be modified to simultaneously or serially acquire, e.g., two photon fluorescence images, by providing at least one additional excitation laser of the appropriate wavelength and at least one additional image sensor or camera, where the at least one additional excitation beam and at the emitted two photon fluorescence are coupled with the SRS imaging system using a combination of dichroic reflectors, beam splitters, etc.

Image processing and image interpretation: In some instances, the disclosed imaging methods may comprise the use of image processing and/or image interpretation algorithms for processing the acquired images and providing qualitative and/or quantitative measures derived from the signals associated with one or more cell-associated contrast agents and/or signals derived from non-fluorescence imaging modalities. In some instances, the image processing and/or image interpretation algorithm may process images acquired using a first imaging modality, e.g., a first optically-sectioned imaging modality, to identify cells and determine their locations. In some instances, the image processing and/or image interpretation algorithm may process images acquired using a second imaging modality that is different from the first, e.g., a second optically-sectioned imaging modality, to identify cells and determine their locations. In some instances, the image processing and/or image interpretation algorithm may process images acquired using either or both of a first and second imaging modalities to identify cells and determine their locations.

In some instances, the image interpretation algorithm may comprise any of a variety of conventional image processing algorithms known to those of skill in the art. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), and mathematical analysis algorithms (e.g., Fourier transform, fast Fourier transform, wavelet analysis, auto-correlation, etc.), or any combination thereof. In some instances, such image processing algorithms may be used to detect individual cells within an image based on, for example, feature size, shape, pattern, intensity, or any combination thereof.

In some instances, the image interpretation algorithm may comprise an artificial intelligence or machine learning algorithm trained, e.g., to further refine the ability of the image processing and/or image interpretation algorithm to identify individual cells within an image and/or to differentiate between normal and non-normal tissue (e.g., neoplastic tissue) based on qualitative and/or quantitative measures that are derived from the signals derived from one or more contrast agents and/or signals derived from non-fluorescence imaging modalities. Any of a variety of machine learning algorithms may be used in implementing the disclosed methods and systems. Examples include, but are not limited to, a supervised learning algorithm, an unsupervised learning algorithm, a semi-supervised learning algorithm, a deep learning algorithm, or any combination thereof. In some instances, the machine learning algorithm may comprise an artificial neural network algorithm, a deep convolutional neural network algorithm, a deep recurrent neural network, a generative adversarial network, a support vector machine, a hierarchical clustering algorithm, a Gaussian process regression algorithm, a decision tree algorithm, a logistical model tree algorithm, a random forest algorithm, a fuzzy classifier algorithm, a k-means algorithm, an expectation-maximization algorithm, a fuzzy clustering algorithm, or any combination thereof.

As a non-limiting example, in some instances, the machine learning algorithm used to further refine the ability of the image processing and/or image interpretation algorithm to identify individual cells within an image and/or to differentiate between normal and non-normal tissue (e.g., neoplastic tissue) may comprise an artificial neural network (ANN), e.g., a deep learning algorithm. Artificial neural networks generally comprise an interconnected group of "nodes" (or "neurons") organized into multiple layers. A typical ANN architecture may comprise an input layer, at least one or more hidden layers, and an output layer. The ANN may comprise any total number of layers, and any number of hidden layers, where the hidden layers function as trainable feature extractors that allow mapping of a set of input data to an output value or a set of output values. As noted, each layer of the neural network comprises a plurality of nodes. A node receives input that comes either directly from the input data (e.g., raw image data and/or pre-processed image data) or the output of nodes in previous layers, and performs a specific operation, e.g., a summation operation. In some cases, a connection from an input to a node is associated with a weight (or weighting factor). In some cases, for example, the node may sum up the products of all pairs of inputs, $x_i$ and their associated weights, $w_i$. In some cases, the weighted sum is offset with a bias, b. In some cases, the output of a neuron may be gated using a threshold or activation function, $f$, which may be a linear or non-linear function. The activation function may be, for example, a rectified linear unit (ReLU) activation function or other function such as a saturating hyperbolic tangent, identity, binary step, logistic, arcTan, softsign, parameteric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, can be "taught" or "learned" in a training phase using one or more sets of training data. For example, the parameters may be trained using the input data from a training data set (e.g., raw image data and/or pre-processed image data) and a gradient descent or backward propagation method so that the output value(s) (e.g., a classification of a given tissue specimen as comprising neoplastic tissue) that the ANN computes are consistent with the examples included in the training data set.

In some instances, the machine learning algorithm may be trained using one or more training data sets that comprise, for example, imaging data acquired for archived histopathological tissue samples (e.g., formalin-fixed tissue samples or fresh frozen tissue samples), imaging data acquired for fresh histopathological tissue samples, or any combination thereof. In some instances, the training data set may be continuously, periodically, or randomly updated with imaging data acquired by two or more systems that have been deployed for use at the same or different sites. In some instances, the two or more systems are deployed at different sites, and the training data set optionally resides in a cloud-based database and/or is continuously, periodically, or randomly updated via an internet connection.

As noted, in some instances, the image interpretation algorithm provides a "cellularity score", e.g., a determination of the number of cells (or cell nuclei) that are identified per unit area of the imaged sample. In some instances, the image interpretation algorithm provides an average signal derived from the cell-associated contrast agent. In some instances, the image interpretation algorithm provides an average signal for the contrast-positive cells after subtracting out a background signal averaged over the entire image. In some instances, the image interpretation algorithm provides the number of cells for which the signal is greater than a specified signal threshold that defines a contrast-positive cell. In some instances, the image interpretation algorithm provides the percentage of total cells in the image that are contrast-positive. As noted above, in some instances, the image interpretation algorithm may be configured to generate quantitative measures based on the signal(s) derived from one or more cell-associated contrast agents and/or signals derived from a second imaging modality, e.g., a non-fluorescence imaging modality such as SRS or one of the other non-fluorescence imaging modalities described herein.

In some instances, the imaging methods and systems of the present disclosure may comprise the use of a pseudo-color algorithm to convert images acquired using any of one or more imaging modalities to generate multicolor images that provide, e.g., enhanced contrast for tissue structure, that provide for enhanced detection of, e.g., neoplastic tissue, and/or that facilitate human interpretation of the image. In some instances, the use of a pseudo-color algorithm to convert images acquired using any of one or more imaging modalities may facilitate human interpretation of the image(s) without the need for implementing additional image interpretation algorithms. In some instances, the pseudo-color images generated from images acquired using any of one or more imaging modalities may then may be combined (e.g., subjected to linear or non-linear algebraic manipulations) to provide for, e.g., enhance contrast for tissue structure, that provide for enhanced detection of, e.g., neoplastic tissue, and/or that facilitate human interpretation of the image.

Software and computer-readable media: Various aspects of the disclosed algorithms (or computer-implemented methods) may be thought of as "products" or "articles of manufacture", e.g., "computer program or software products", typically in the form of processor executable code and/or associated data that is stored in a type of computer readable medium, where the processor executable code comprises a plurality of instructions for controlling a computer or computer system in performing one or more of the methods disclosed herein. Thus, disclosed herein are computer-readable media ("computer program or software products") comprising a set of encoded instructions (i.e., software) which, when executed by a processor direct the processor to perform a series of logical steps to perform any of the methods disclosed herein. For example, disclosed herein are computer-readable media ("computer program or software products") comprising a set of encoded instructions (i.e., software) which, when executed by a processor directs the processor to perform a series of logical steps to: (i) acquire images using one or more of the imaging modalities disclosed herein, (ii) perform manual, semi-automated, or automated processing of the acquired images to identify one or more individual cells therein, (iii) perform manual, semi-automated, or automated further processing of the acquired images to extract quantitative measures of signals derived from cell-associated contrast agents at the locations of the one or more individual cells, (iv) perform manual, semi-automated, or automated further processing of the acquired images to extract quantitative measures of signals derived from non-fluorescence images of the same tissue specimen at the location(s) of the one or more individual cells, or (v) any combination thereof.

Processor-executable (or machine-executable) code may be stored, for example, in an optical storage unit comprising an optically-readable medium such as an optical disc, CD-ROM, DVD, or Blu-Ray disc. Processor-executable code may be stored in an electronic storage unit, such as memory (e.g., read-only memory, random-access memory, flash memory) or on a hard disk. "Storage" type media include any or all of the tangible memory of a computer, computer system, etc., or associated modules thereof, such as various semiconductor memory chips, optical drives, tape drives, disk drives, and the like, which may provide non-transitory storage at any time for the software that encodes the methods and algorithms disclosed herein.

All or a portion of the software code may at times be communicated via the Internet or various other telecommunication networks. Such communications, for example, may enable loading of the software from one computer or processor into another, e.g., from a management server or host computer into the computer platform of an application server. Thus, other types of media that may be used to convey the software encoded instructions include optical, electrical, and electromagnetic waves, such as those used across physical interfaces between local devices, through wired and optical landline networks, and over various atmospheric telecommunication links. The physical elements that carry such waves, such as wired or wireless links, optical links, or the like, are also considered media that convey the software encoded instructions for performing the methods disclosed herein.

Computer processors: In some instance, the disclosed imaging systems may comprise one or more processors or computers that are individually or collectively programmed to provide instrument control and/or image processing functionality according to the methods disclosed herein. The one or more processors may comprise a hardware processor such as a central processing unit (CPU), a graphic processing unit (GPU), a general-purpose processing unit, or computing platform. The one or more processors may be comprised of any of a variety of suitable integrated circuits (e.g., application specific integrated circuits (ASICs), or field-programmable gate arrays (FPGAs)), microprocessors, emerging next-generation microprocessor designs (e.g., memristor-based processors), logic devices, and the like. Although the disclosure is described with reference to a processor, other types of integrated circuits and logic devices may also be applicable. The processor may have any suitable data operation capability. For example, the processor may perform 512 bit, 256 bit, 128 bit, 64 bit, 32 bit, or 16 bit data operations. The one or more processors may be single core or multi core processors, or a plurality of processors configured for parallel processing.

In some instances, the one or more processors or computers used to implement the disclosed imaging methods may be part of a larger computer system and/or may be operatively coupled to a computer network (a "network") with the aid of a communication interface to facilitate transmission of and sharing of data. The network may be a local area network, an intranet and/or extranet, an intranet and/or extranet that is in communication with the Internet, or the Internet. The network in some cases is a telecommunications and/or data network. The network may include one or more computer servers, which in some cases enables distributed computing, such as cloud computing. The network, in some cases with the aid of the computer system, may implement a peer-to-peer network, which may enable devices coupled to the computer system to behave as a client or a server.

In some instances, the disclosed imaging systems may also include memory or memory locations (e.g., random-access memory, read-only memory, flash memory, etc.), electronic storage units (e.g., hard disks), communication interfaces (e.g., network adapters) for communicating with one or more other imaging systems and/or peripheral devices such as data storage and/or electronic display adapters.

In some instance, the data storage units store files, such as drivers, libraries, and saved programs. The storage units may also store user data, e.g., user-specified preferences, user-specified programs, and image data acquired during the testing or use of the disclosed imaging systems. The computer system or network in some cases may include one or more additional data storage units that are external to the computer system, such as data storage units located on a remote server that is in communication with the computer system through an intranet or the Internet.

EXAMPLES

These examples are provided for illustrative purposes only and not to limit the scope of the claims provided herein.

Example 1—Two Photon Fluorescence Imaging of Brain Tissue Dosed with 5-ALA

Figure 2:
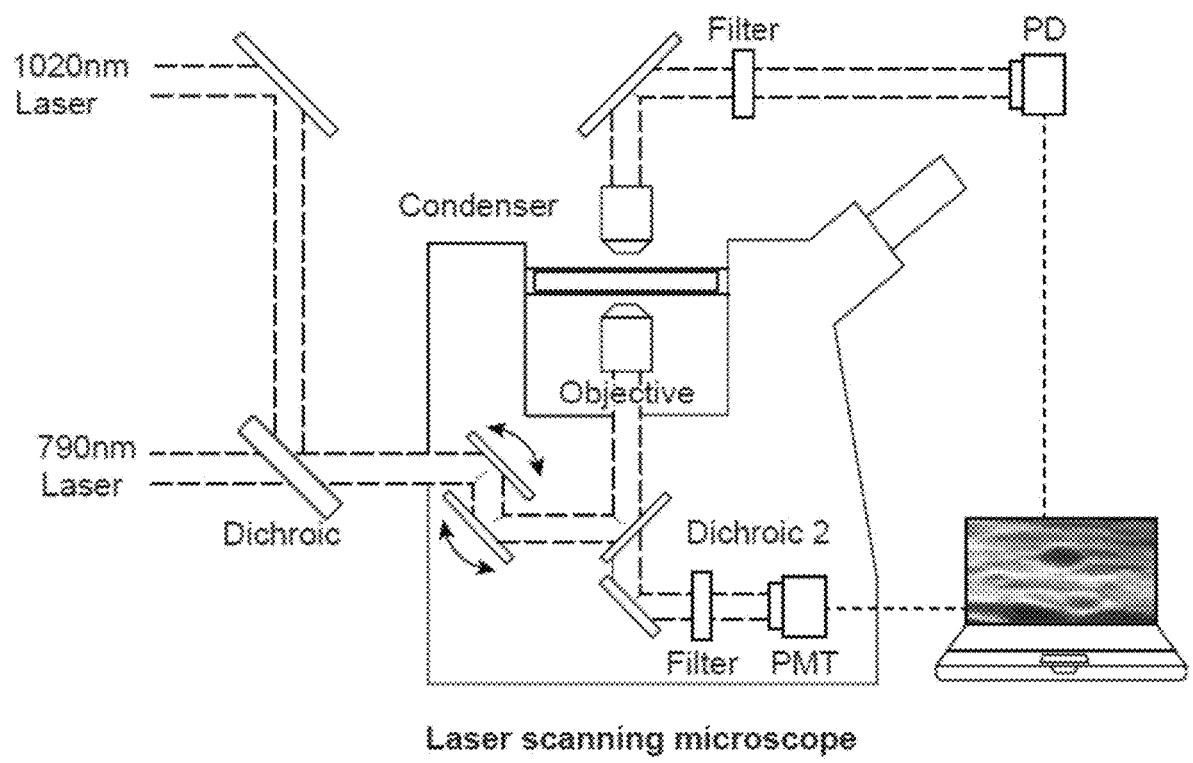
FIG. 2 provides a schematic illustration of a high-resolution optical microscope that combines stimulated Raman scattering (SRS) microscopy to image tissue morphology with two-photon fluorescence (2P) microscopy to image the distribution of fluorescence contrast agents.
Figure 3A:
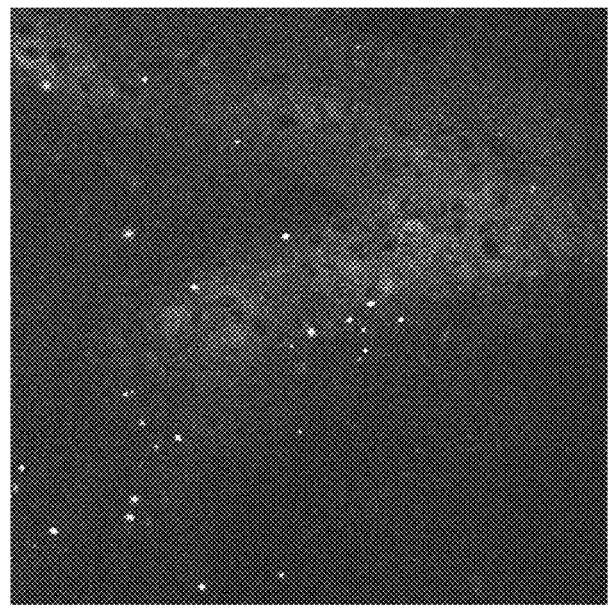
FIG. 3A provides a non-limiting example of a two-photon fluorescence image of a brain tumor tissue sample dosed with 5-ALA as a contrast agent.
Figure 3B:
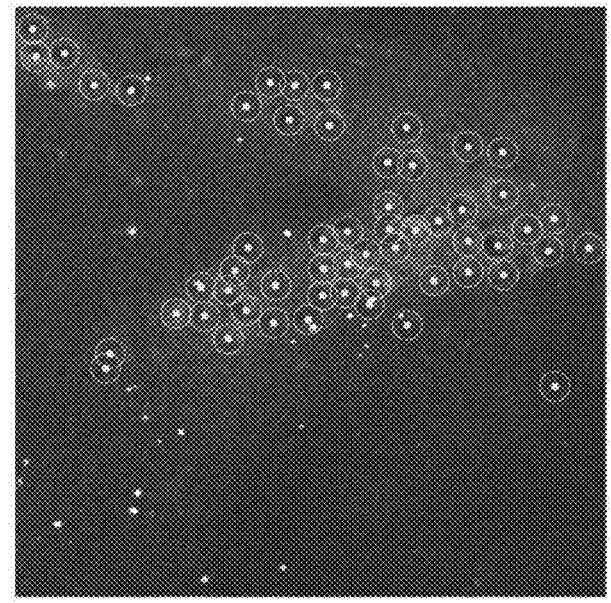
FIG. 3B provides a non-limiting example of the two-photon fluorescence image of the brain tumor tissue sample shown in FIG. 3A after processing the image to identify individual cells in the image.

We used the 2P imaging mode of the combined 2P/SRS microscope illustrated in FIG. 2 with two excitation beams of wavelengths 790 nm and 1020 nm, respectively, and a 640 nm/80 nm bandpass detection filter to image an ex vivo specimen of brain tumor tissue dosed with 5-ALA as the contrast agent (FIG. 3A). FIG. 3B shows the same two-photon fluorescence image of the brain tumor tissue sample shown in FIG. 3A after processing the image to identify individual cells in the image (circles). To our knowledge, this is the first time that individual cancer cells have been visualized in tissue based on 5-ALA and constitutes a breakthrough in detection sensitivity. We were able to resolve individual cells and have found that the contrast agent accumulates in the cell cytoplasm and does not penetrate the cell nucleus.

We have also found that individual highly fluorescent granules can also be seen (FIG. 3A). To our surprise, these were still visible in control samples from tissue that was not dosed with 5-ALA, and accordingly have been attributed to auto-fluorescent background.

Figure 4A:
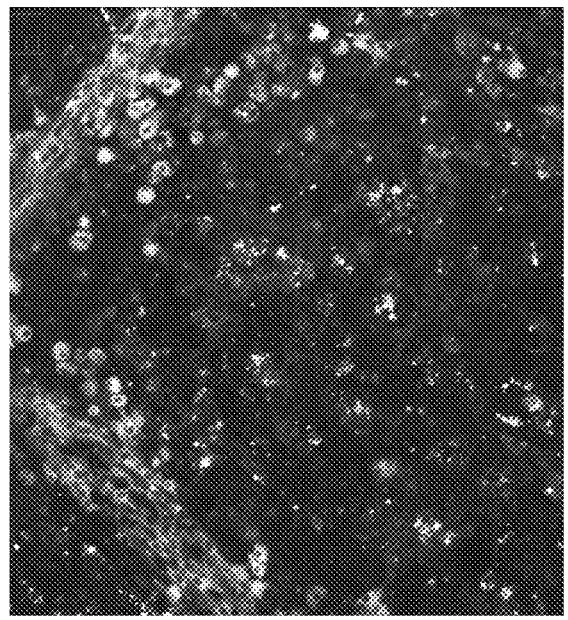
FIG. 4A provides a non-limiting example of an ex vivo two-photon fluorescence image of biopsy tissue from a patient dosed with 5-ALA as a contrast agent.
Figure 4B:
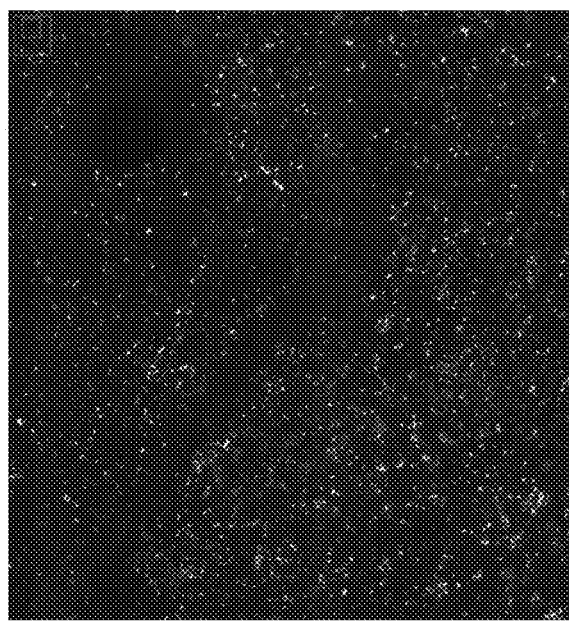
FIG. 4B provides a non-limiting example of an ex vivo two-photon fluorescence image of biopsy tissue from a patient that was not dosed with a contrast agent.

When expanding the evaluation to in vivo imaging of human tissue specimens (e.g., FIG. 4A; brain tissue for a patient dosed with 5-ALA) with our 2-photon microscope, we experienced a similar unexpected non-specificity of the contrast mechanism where 640 nm fluorescent signal was also detected in tissue specimens from patients that had not been given the 5-ALA contrast agent (FIG. 4B). Specifically, one can see in FIG. 4B that the cell-associated fluorescent signal and general "haze" visible in FIG. 4A is not visible in the patient that has not been given the contrast agent, but fluorescent granules are visible in both cases.

Figure 5:
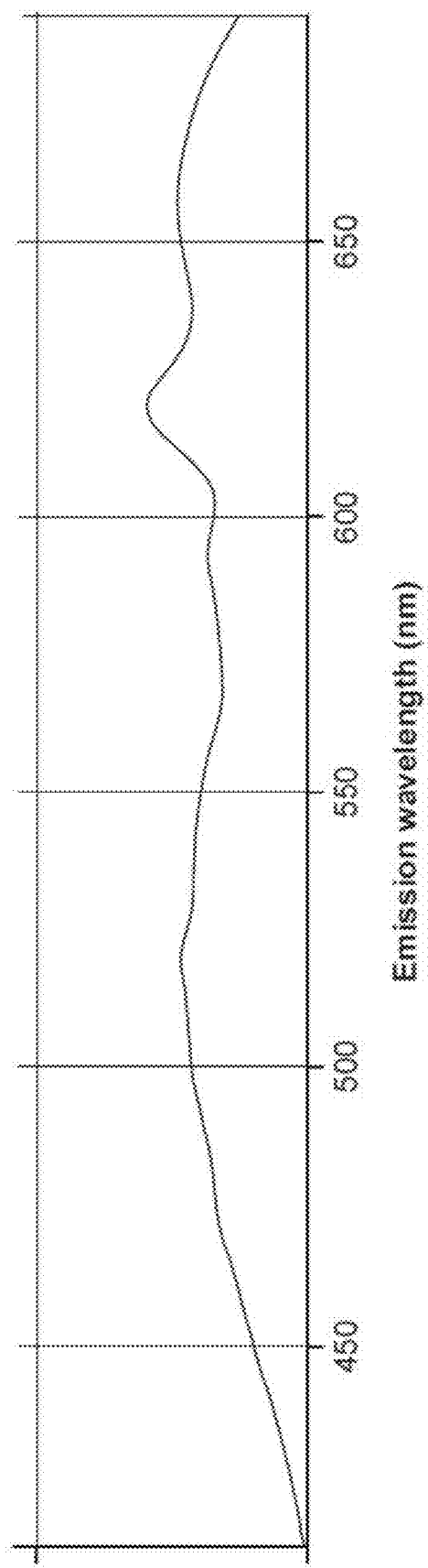
FIG. 5 provides a non-limiting example of the two-photon fluorescence emission spectrum for a brain tissue sample dosed with 5-ALA as a contrast agent.

This came as a surprise, since this non-specificity had not been disclosed in previous work for imaging contrast using regular (1-photon fluorescence) surgical microscopes. In fact, the United States FDA has approved this contrast agent for clinical use based on data that shows excellent sensitivity. We hypothesize that such non-specificity may be due to the nature of 2-photon excitation, which is known to be less specific. We investigated the 2-photon emission spectrum of a brain tumor tissue specimen dosed with 5-ALA and found that the characteristic spectral peak of 5-ALA (between 620 nm and 650 nm) was indeed present on top of a large and spectrally-broad background signal (FIG. 5).

Figure 6:
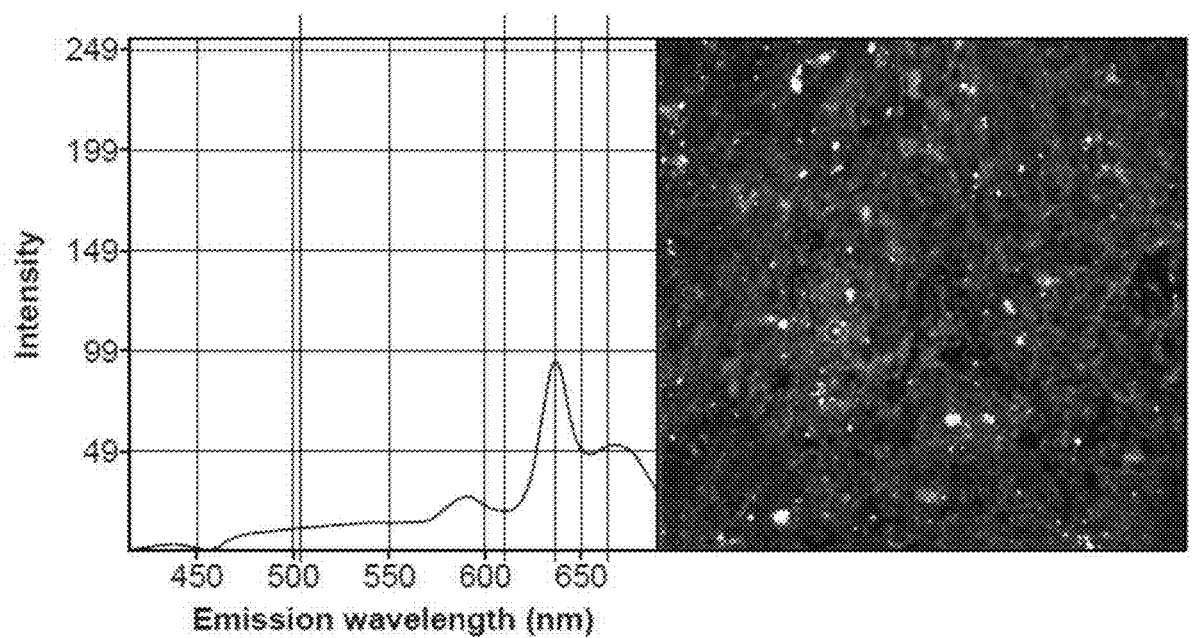
FIG. 6 provides a non-limiting example of a one-photon fluorescence emission spectrum (left) obtained for a tissue sample (image at right) dosed with 5-ALA.

We therefore set out to image the specimen with a 1-photon confocal fluorescence microscope. When the specimen was imaged using an open pinhole (FIG. 6, right), i.e., without significant optical sectioning, we recovered the excellent specificity of the contrast agent, where the emission peak is visible without the large and spectrally-broad background (FIG. 6, left). However, when we closed the pinhole in order to create the optical sectioning (i.e., the reduced depth of field) required to image single cells within a thick, un-sectioned tissue specimen, this spectral specificity was lost and only spectrally-broad granules were visible, just as was observed in the 2-photon image. We hypothesize that this may be due to increased photo-bleaching found in 1-photon excitation at the focal plane, where the photon flux is the highest and the contrast agent is bleached must faster compared to the background signal. Therefore, cellular imaging of a contrast agent (like 5-ALA) using 2P imaging, as opposed to macroscopic imaging (e.g., with a conventional surgical microscope), faces the dilemma that 2P imaging can provide the sensitivity to image single contrast-positive cells but is intrinsically less specific, while 1P imaging suffers from photobleaching in the focal plane and therefore suffers from limited sensitivity or reduced imaging speed. In either case, a measurement of fluorescent intensity averaged over the image will not provide an accurate read of the tumor burden in the image.

Example 2—Dual-Mode Imaging for Increased Sensitivity and Specificity

This example combines SRS microscopy to image the tissue morphology with 2P microscopy to image the distribution of a fluorescent contrast agent (FIG. 2). A dual-wavelength fiber laser system (producing light at, e.g., 1020 nm and 790 nm) was used to excite the specimen and detect the SRS signal in transmission with a photodetector (PD). We also detect the 2P signal in reflection with a second photodetector (e.g., a photomultiplier (PMT)) after blocking the excitation light with a filter. Images were acquired by scanning the laser focus through the sample point-by-point with a galvo scan mirror controlled from a computer. In such a multi-modal microscope, both SRS and 2P images can be acquired simultaneously.

Figure 7:
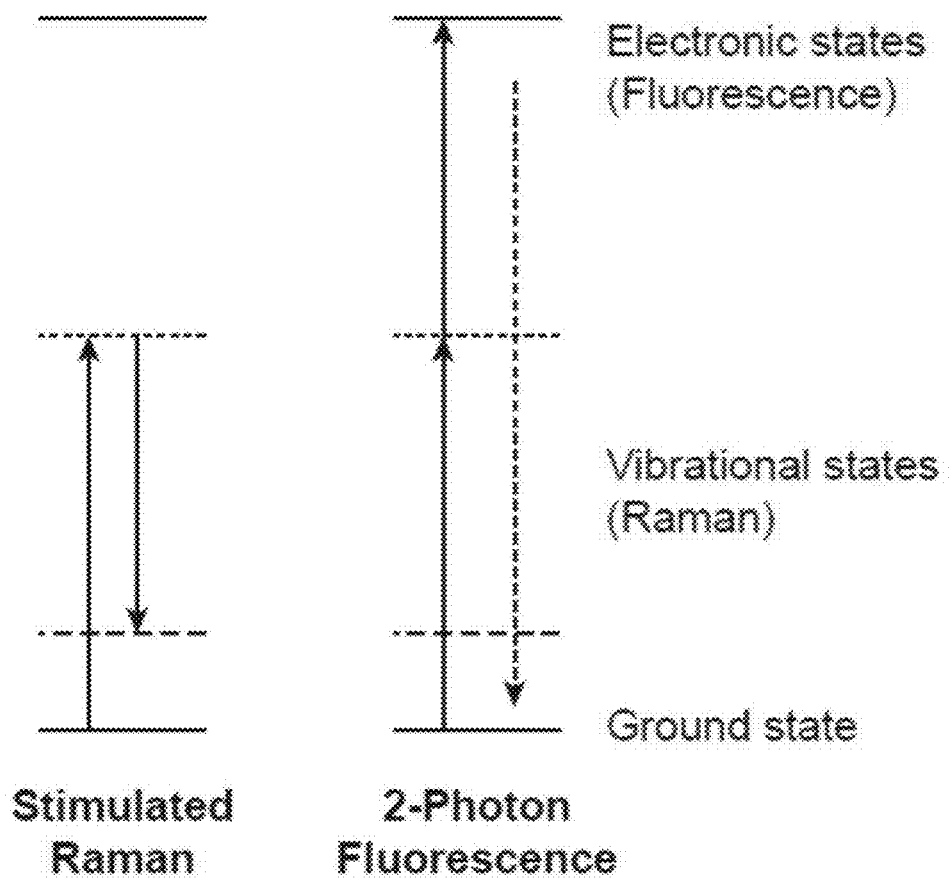
FIG. 7 provides a schematic illustration of the energy level diagram and ground state to vibrational or electronic state transitions that occur for the stimulated Raman and two-photon fluorescence processes.

Energy level diagrams for the two techniques are shown in FIG. 7. In SRS, the molecule is excited from the ground state to a vibration state based on the stimulated excitation by a pump photon (FIG. 7, left, upward arrow) and Stokes photon (FIG. 7, left, downward arrow) if the energy difference matches that of a molecular vibration. In 2P, electronic states of the contrast agent are excited by simultaneous absorption of two photons (e.g., two pump photons, or two Stokes photons, or one pump and one Stokes photon) (FIG. 7, right, upward arrows) and the molecule subsequently relaxes back to the ground state while emitting a fluorescent photon that can be detected (FIG. 7, right, downward arrows).

Figure 8A:
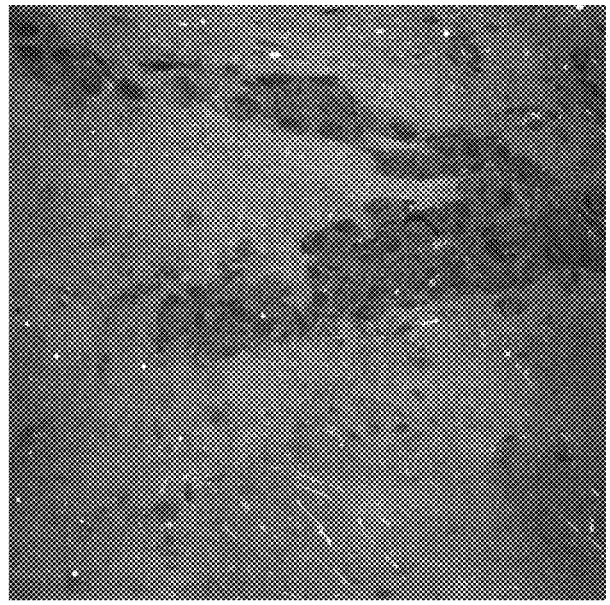
FIG. 8A provides a non-limiting example of a stimulated Raman scattering image of a brain cancer tissue specimen.

The image in FIG. 8A shows an SRS image of a brain cancer tissue specimen at the $CH_2$-vibration frequency of lipids (e.g., 2850 $cm^{-1}$). At this wavenumber, the image has positive signal for cytoplasm and intercellular space and nuclei are dark (due to lack of lipids). This contrast can be used to positively identify cells based on identification of the nuclei using information comprising, e.g., the size, shape, pattern, and/or signal strength of features in the image. It can be advantageous to image the same tissue at the $CH_3$-vibrational frequency of protein and nucleic acids (e.g. at 2930 $cm^{-1}$) to provide additional contrast for nuclei. The SRS imaging channel is independent of the contrast agent (2P fluorescence) imaging channel. Other label-free approaches to imaging such as CARS, CR, or THG can also be used as an alternative imaging modality to SRS.

Figure 8B:
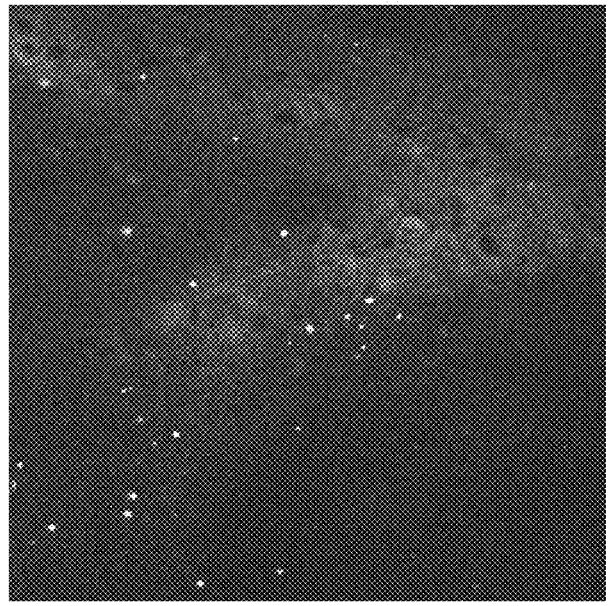
FIG. 8B provides a non-limiting example of a two-photon fluorescence image that shows the distribution of a contrast agent (5-ALA) in the same brain cancer tissue specimen as that depicted in FIG. 8A.

The image in FIG. 8B shows the 2P fluorescence microscope image of the distribution of 5-ALA contrast agent acquired as discussed above at the same location as FIG. 8A. Comparing the two images shows that some but not all cells identified based on the SRS images also have positive cellular signal in the fluorescent channel.

Figures 9A, 9B:
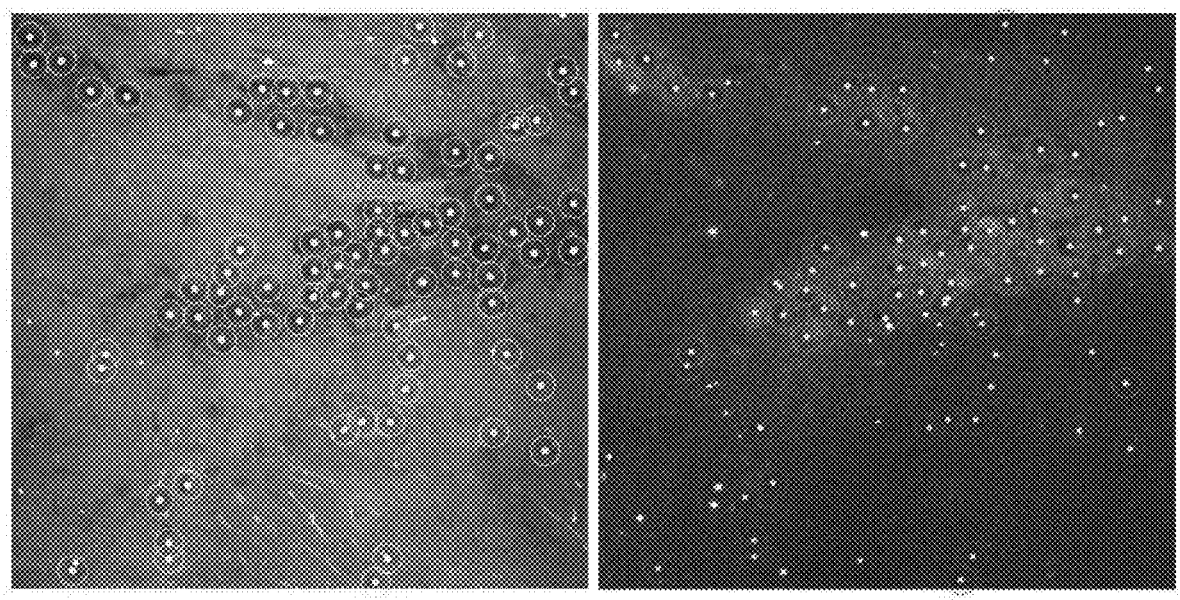
FIG. 9A illustrates the automated detection of nuclei or cells (circled) in the stimulated Raman scattering image of FIG. 8A.
FIG. 9B illustrates the automated measurement of fluorescence intensities within specified cellular areas (circled) that are centered on the nuclei or cells detected in the image shown in FIG. 8B.

The imaging system can use automated image processing to determine the location and/or size of nuclei or cells from the SRS image (FIG. 9A, circles) to measure the fluorescence intensity within the individual cell areas (FIG. 9B, circles) to provide a measure of the fluorescence signal arising from cell-associated contrast agent. It is also possible to determine if the fluorescence signal within a selected area is above a specified threshold level and provide a binary output of whether a particular cell is positive or negative for the contrast agent. This allows determination of a quantitative measure of the percentage of contrast agent positive cells within an image.

In some instances, the disclosed imaging systems may provide high-resolution, optically-sectioned Raman images at wavenumbers of both 2,850 cm-1 and 2,930 $cm^{-1}$. In addition to these images, the disclosed imaging systems may provide high-resolution, optically-sectioned images of one or more fluorescence channels (emission wavelength ranges). Using the Raman data, the image interpretation algorithm is able to spatially identify characteristics of cells and determine a cellularity score. Combining these metrics and data with the fluorescence channels as input to the image interpretation algorithm creates a set of metrics correlating the fluorescence data with the Raman data. Examples of these metrics include, but are not limited to, a number of cells identified, a number of cells associated with positive fluorescence, a percentage of cells associated with positive fluorescence, a ratio of positive fluorescence cells to negative fluorescence cells, and a ratio of positive fluorescence cells to total cells, or any combination thereof.

Example 3—Dual Wavelength Fluorescence Imaging

In this example, the imaging system is a multi-channel 2P microscope that simultaneously acquires a first fluorescence image at the emission wavelength of the contrast agent (e.g., at 640 nm±40 nm for 5-ALA) and a second fluorescence image outside the emission wavelength of the contrast agent (e.g., at <600 nm for 5-ALA) as a measure of non-specific background. It is then possible to provide the multi-channel emission signals to an image processing or image interpretation algorithm and suppress the non-specific background signal based on the measured spectral characteristics of the contrast agent-specific and background signals (e.g. by ratio or thresholding). As noted above, it is possible to create multi-color images based on applying a pseudo-coloring algorithm to the multi-channel image data to facilitate human interpretation of the image in real- or near-real time.

Figure 10A:
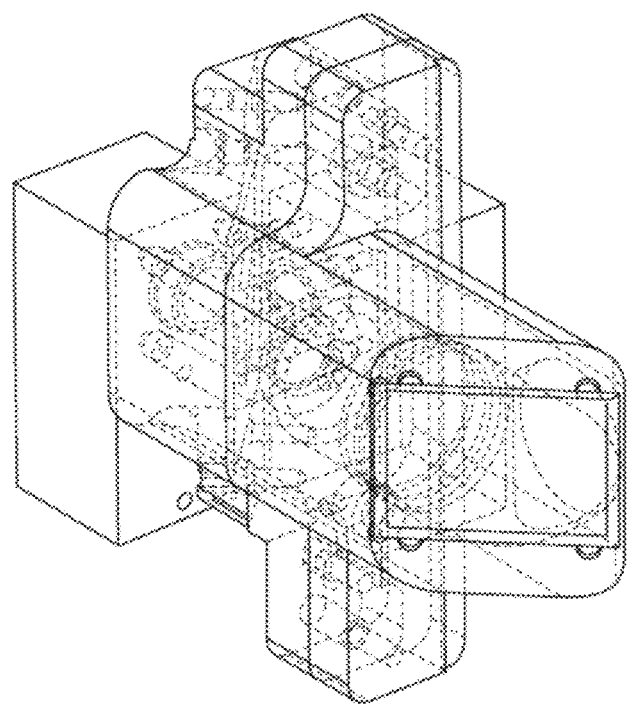
FIG. 10A provides a first view of a dual-channel, non-descanned detector design comprising a dichroic filter that is used to separate emission bands and direct signals towards different photomultiplier tubes (PMTs) that may be individually filtered to detect a specific emission band.
Figure 10B:
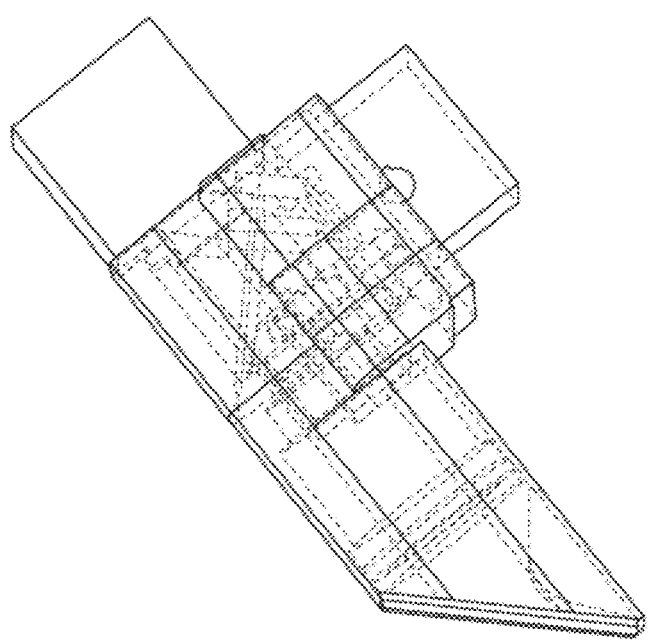
FIG. 10B provides a second view of the dual-channel, non-descanned detector design illustrated in FIG. 10A.

An example of a dual-channel non-descanned (external) detector design for collecting fluorescence signals in two different emission wavelength ranges is shown in FIG. 10A and FIG. 10B, where a dichroic filter is used to separate the emission bands and direct the signal toward two photomultiplier tubes (PMTs) that are individually filtered to detect the respective emission bands. This design can be expanded to include additional detectors (>2) to further improve sensitivity and specificity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A system for imaging a tissue specimen comprising:
a) a first optical sub-system configured to acquire high-resolution images of a distribution of a contrast agent within the tissue specimen using a first optical-sectioning imaging modality;
b) a second optical sub-system configured to acquire high-resolution images of tissue specimen morphology using a second optical-sectioning imaging modality, wherein the first and second optical sub-systems are configured to image a same optical plane within the tissue specimen; and
c) a processor configured to: (i) process the high-resolution images of the distribution of the contrast agent and/or the high resolution images of the tissue specimen morphology to identify individual cells and— determine locations of the individual cells;
(ii) process the high-resolution images of the distribution of the contrast agent to derive a signal from the contrast agent at the locations of the individual cells; (iii) measure a background value from the high-resolution images of the distribution of the contrast agent at the locations of the individual cells; (iv) correct the signal from the contrast agent at the locations of the individual cells using the background value; and (v) output a quantitative measure of the signal from the contrast agent.

2. The system of claim 1, wherein the first optical-sectioning imaging modality comprises two-photon fluorescence microscopy, confocal fluorescence microscopy, light sheet microscopy, or structured illumination microscopy.

3. The system of claim 1, wherein the second optical-sectioning imaging modality comprises stimulated Raman scattering microscopy, coherent anti-Stokes Raman scattering microscopy, confocal reflection microscopy, second harmonic generation microscopy, or third harmonic generation microscopy.

4. The system of claim 3, wherein the second optical-sectioning imaging modality comprises stimulated Raman scattering microscopy, and wherein the second optical sub-system is configured to acquire the high-resolution images of tissue specimen morphology at a wavenumber of 2,850 cm$^{-1}$ corresponding to $CH_2$-vibration of lipid molecules.

5. The system of claim 4, wherein the second optical sub-system is further configured to acquire the high-resolution images of tissue specimen morphology at a wavenumber of 2,930 cm$^{-1}$ corresponding to $CH_3$-vibration of protein and nucleic acid molecules.

6. The system of claim 1, wherein the first and second optical sub-systems are configured to have an axial resolution smaller than 10 µm.

7. The system of claim 1, wherein the first and second optical sub-systems are configured to have a lateral resolution smaller than 5 µm.

8. The system of claim 1, wherein the first optical sub-system is further configured to acquire the high-resolution images of the distribution of the contrast agent in a first detection wavelength range and in a second detection wavelength range.

9. The system of claim 8, wherein:
the first detection wavelength range includes an emission peak of the contrast agent; and
the second detection wavelength range excludes the emission peak of the contrast agent,
wherein the first detection wavelength range includes 640 nm light, and the second detection wavelength range includes wavelengths shorter than 600 nm; and
wherein the processor is configured to compare the high-resolution images of the distribution of the contrast agent in the first detection wavelength range and the high-resolution images of the distribution of the contrast agent in the second detection wavelength range to measure the background value.

10. The system of claim 9, wherein the contrast agent comprises 5-aminolevulinic acid (5-ALA).

11. The system of claim 1, wherein the contrast agent comprises fluorescein, 5-ALA, BLZ-100, or LUM015.

12. The system of claim 1, wherein the processor is configured to identify the individual cells and determine the locations of the individual cells based on one or more image features, wherein the one or more image features comprise size, shape, pattern, intensity, or any combination thereof.

13. The system of claim 1, wherein the processor is configured to run a machine learning algorithm, wherein the machine learning algorithm is configured to identify individual cells in the high resolution images of tissue specimen morphology based on computational parameters acquired from a training data set comprising imaging data acquired for archived histopathological tissue samples, imaging data acquired for fresh histopathological tissue samples, or any combination thereof.

14. The system of claim 13, wherein the processor is configured to continuously, periodically, or randomly update the training data set.

15. The system of claim 1, wherein the processor is further configured to determine a total or an average intensity of the quantitative measure of the signal from the contrast agent.

16. The system of claim 1, wherein the processor is configured to determine whether the signal from the contrast agent is above a specified threshold level for contrast-positive cells.

17. The system of claim 16, wherein the quantitative measure comprises a measure of a total number of the contrast-positive cells, a density of the contrast-positive cells, a percentage of the contrast-positive cells, or any combination thereof, in the high-resolution images of tissue specimen morphology.

18. The system of claim 17, wherein the processor is further configured to output a cellularity score based on the high-resolution images of tissue specimen morphology.

19. The system of claim 1, wherein the high-resolution images of the distribution of the contrast agent and the high-resolution images of tissue specimen morphology comprise in vivo images of the tissue specimen.

* * * * *

UNITED STATES PATENT AND TRADEMARK OFFICE
CERTIFICATE OF CORRECTION

| | | |
|---|---|---|
| PATENT NO. | : 12,161,486 B2 | Page 1 of 1 |
| APPLICATION NO. | : 17/491844 | |
| DATED | : December 10, 2024 | |
| INVENTOR(S) | : Christian Wilhelm Freudiger et al. | |

It is certified that error appears in the above-identified patent and that said Letters Patent is hereby corrected as shown below:

In the Claims

In Claim 1, at Column 32, Line 2, please delete the "—" after "individual cells and"
In Claim 1, at Column 32, Line 4, please move the "(ii)" to the line above and remove the indent, so that "(ii)" is formatted consistently with formatting of "(i)", "(iii)", "(iv)", and "(v)"

Signed and Sealed this
Tenth Day of June, 2025

Coke Morgan Stewart
*Acting Director of the United States Patent and Trademark Office*